(12) United States Patent
Ono et al.

(10) Patent No.: US 9,574,182 B2
(45) Date of Patent: Feb. 21, 2017

(54) MONOTERPENE GLYCOSYLTRANSFERASE ORIGINATING FROM HOP AND METHOD FOR USING SAME

(71) Applicant: SUNTORY HOLDINGS LIMITED, Osaka (JP)

(72) Inventors: Eiichiro Ono, Osaka (JP); Nobuo Tsuruoka, Osaka (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 72 days.

(21) Appl. No.: 14/376,463

(22) PCT Filed: Feb. 5, 2013

(86) PCT No.: PCT/JP2013/053166
§ 371 (c)(1),
(2) Date: Aug. 4, 2014

(87) PCT Pub. No.: WO2013/118906
PCT Pub. Date: Aug. 15, 2013

(65) Prior Publication Data
US 2015/0140132 A1   May 21, 2015

(30) Foreign Application Priority Data

Feb. 6, 2012   (JP) ................. 2012-022982

(51) Int. Cl.
| | |
|---|---|
| *C12N 9/10* | (2006.01) |
| *A61Q 13/00* | (2006.01) |
| *A61K 31/7028* | (2006.01) |
| *C12N 15/82* | (2006.01) |
| *C11B 9/00* | (2006.01) |
| *C12P 19/18* | (2006.01) |
| *C12P 19/44* | (2006.01) |
| *A61K 8/64* | (2006.01) |
| *A61K 36/00* | (2006.01) |
| *A61K 38/00* | (2006.01) |

(52) U.S. Cl.
CPC ......... *C12N 9/1051* (2013.01); *A23L 27/2052* (2016.08); *A23L 27/36* (2016.08); *A23L 33/17* (2016.08); *A61K 8/64* (2013.01); *A61K 31/7028* (2013.01); *A61Q 13/00* (2013.01); *C11B 9/0003* (2013.01); *C12N 15/8243* (2013.01); *C12N 15/8245* (2013.01); *C12P 19/18* (2013.01); *C12P 19/44* (2013.01); *A61K 36/00* (2013.01); *A61K 38/00* (2013.01); *Y02P 20/52* (2015.11)

(58) Field of Classification Search
CPC .................................................. C12N 9/1051
See application file for complete search history.

(56) References Cited

U.S. PATENT DOCUMENTS

| | | | |
|---|---|---|---|
| 2005/0277766 A1 | 12/2005 | Möller et al. | |
| 2006/0275877 A1 | 12/2006 | Hansen et al. | |
| 2010/0143975 A1 | 6/2010 | Caputi et al. | |

FOREIGN PATENT DOCUMENTS

| | | |
|---|---|---|
| JP | 3-193712 | 8/1991 |
| JP | 9-67245 | 3/1997 |
| JP | 2002-058450 | 2/2002 |
| WO | 97/11184 | 3/1997 |

OTHER PUBLICATIONS

Guo et al. 2004, PNAS 101(25) pp. 9205-9210.*
Noguchi et al., "cDNA Cloning of Glycosyltransferases from Chinese Wolfberry (*Lycium barbarum* L.) Fruits and Enzymatic Synthesis of a Catechin Glucoside Using a Recombinant Enzyme (UGT73A10)", *Journal of Molecular Catalysis B: Enzymatic*, vol. 55, No. 1-2, pp. 84-92, 2008.
Van Bakel et al., "The Draft Genome and Transcriptome of *Cannabis sativa*", *Genome Biology*, vol. 12, No. 10, pp. 1-17, 2011.
Nagatoshi et al., "Iridoid-specific Glucosyltransferase from *Gardenia jasminoides*", *The Journal of Biological Chemistry*, vol. 286, No. 37, pp. 32866-32874, 2011.
Kollmannsberger et al., "Glycosidically Bound Flavour Compounds in Hop (*Humulus lupulus* L): 1. Enzymatical Liberation von Aglycones", *Advances in Food Sciences*, vol. 24, No. 3, pp. 106-115, 2002, along with an English language Summary.
Extended European Search Report issued in EP Patent Application No. 13747284.1, dated Dec. 17, 2015.
Kollmannsberger et al., "Occurrence of Glycosidically Bound Flavour Compounds in Hops, Hop Products and Beer," *Brewing Science—Monatsschrift für Brauwissenschaft*, vol. 59, pp. 83-89, 2006.
Fan et al., "Characterization of Three Terpenoid Glycosyltransferase Genes in 'Valencia' Sweet Orange (*Citrus sinensis* L. Osbeck)," *Genome*, vol. 53, No. 10, pp. 816-823, 2010.
Aharoni et al., "Terpenoid Metabolism in Wild-Type and Transgenic Arabidopsis Plants," *The Plant Cell*, vol. 15, pp. 2866-2884, 2003.
Kollmannsberger et al., "Occurrence of Glycosidically Bound Flavour Compounds in Hops, Hop Products and Beer," *Brewing Science—Monatsschrift für Brauwissenschaft*, vol. 59, pp. 83-89, 2006 (Abstract).
Guo et al., "(*S*)-Linalyl, 2-Phenylethyl, and Benzyl Disaccharide Glycosides Isolated as Aroma Precursors from Oolong Tea Leaves," *Biosci. Biotech. Biochem.*, vol. 58, No. 8, pp. 1532-1534, 1994.

(Continued)

*Primary Examiner* — Russell Kallis
(74) *Attorney, Agent, or Firm* — Greenblum & Bernstein, P.L.C.

(57) ABSTRACT

The object of the present invention is to provide *Humulus lupulus*-derived monoterpene glycosyltransferase and a method for producing a monoterpene glycoside by means of this enzyme.

The present invention provides *Humulus lupulus*-derived monoterpene glycosyltransferase and a method for producing a monoterpene glycoside by means of this enzyme. The present invention provides a transformant transformed with a gene for *Humulus lupulus*-derived monoterpene glycosyltransferase and a method for producing such a transformant.

11 Claims, 3 Drawing Sheets

(56) References Cited

OTHER PUBLICATIONS

Nishikitani et al., "Geranyl 6-O-α-L-Arabinopyranosyl-β-D-glucopyranoside Isolated as an Aroma Precursor from Leaves of a Green Tea Cultivar," *Biosci. Biotech. Biochem.*, vol. 60, No. 5, pp. 929-931, 1996.

Moon et al., "*cis*- and *trans*-Linalool 3,7-Oxides and Methyl Salicylate Glycosides and (Z)-3-Hexenyl β-D-Glucopyranoside as Aroma Precursors from Tea Leaves for Oolong Tea," *Biosci. Biotech. Biochem.*, vol. 60, No. 11, pp. 1815-1819, 1996.

Sekiwa et al., "Isolation of Some Glucosides as Aroma Precursors from Ginger," *Biosci. Biotechnol. Biochem.*, vol. 63, No. 2, pp. 384-389, 1999.

Ma, "The (3R,9R)-3-hydroxy-7,8-dihydro-β-ionol Disaccharide Glycoside is an Aroma Precursor in Tea Leaves," *Phytochemistry*, vol. 56, pp. 819-825, 2001.

Mizutani et al., "Cloning of β-Primeverosidase from Tea Leaves, a Key Enzyme in Tea Aroma Formation," *Plant Physiol.*, vol. 130, pp. 2164-2176, 2002.

Nedjma et al., "Beer Flavour Enhancement by Using Exogenous β-1,3,β-1,6-glucanases and β-glucosidase Produced by Solid State Fermentation (SSF)—Impact of Yeast Hybrids on Beer Flavour," *Proceedings of the 31st EBC Congress*, pp. 1-13 2007.

Caputi et al., "Discovery of New Biocatalysts for the Glycosylation of Terpenoid Scaffolds," *Chem. Eur, J.*, vol. 14, pp. 6656-6662, 2008.

Herrmann, "Controlled Release of Volatiles under Mild Reaction Conditions: From Nature to Everyday Products," *Angew. Chem. Int. Ed.*, vol. 46, pp. 5836-5863, 2007.

Winterhalter et al., "Glycoconjugated Aroma Compounds: Occurrence, Role and Biotechnological Transformation," *Advances in Biochemical Engineering/Biotechnology*, vol. 55, pp. 73-105, 1997.

Fan et al., "Characterization of Three Terpenoid Glycosyltransferase Genes in 'Valencia' Sweet Orange (*Citrus sinensis* L. Osbeck)," *Genome*, vol. 53, No. 10, pp. 816-823, 2010 (Abstract).

Taguchi et al., "Nicotiana tabacum NtGT5b mRNA for glycosyltransferase, complete cds," *GenBank*: AB176524.1, Mar. 11, 2009.

\* cited by examiner

SEQUENCE LISTING

```
<160> NUMBER OF SEQ ID NOS: 21

<210> SEQ ID NO 1
<211> LENGTH: 1464
<212> TYPE: DNA
<213> ORGANISM: Humulus lupulus
<220> FEATURE:
<221> NAME/KEY: CDS
<222> LOCATION: (1)..(1461)

<400> SEQUENCE: 1 atg acc atg gaa act aag cct cac gca gta tgc atc cca tac cca gca      48
Met Thr Met Glu Thr Lys Pro His Ala Val Cys Ile Pro Tyr Pro Ala
1               5                   10                  15 cag ggc cat ata agc cct atg ctg aaa ctg gcc aag ctt ctc cac cag      96
Gln Gly His Ile Ser Pro Met Leu Lys Leu Ala Lys Leu Leu His Gln
                20                  25                  30 aga ggc ttc cac ata acc ttc gtc aac acc cac ttc aac cac aac cgt     144
Arg Gly Phe His Ile Thr Phe Val Asn Thr His Phe Asn His Asn Arg
            35                  40                  45 ctc ctc aaa tct aga ggc ccc aac tcc ctc gac ggt ttg cct gat ttt     192
Leu Leu Lys Ser Arg Gly Pro Asn Ser Leu Asp Gly Leu Pro Asp Phe
        50                  55                  60 cgc ttc gaa tca atc ccg gac ggc ctt cct ccg acg gag aac aaa gcc     240
Arg Phe Glu Ser Ile Pro Asp Gly Leu Pro Pro Thr Glu Asn Lys Ala
65                  70                  75                  80 gac gcc acg cag gac atc cca tcc ctg tgc gag tcc acc gaa aag acc     288
Asp Ala Thr Gln Asp Ile Pro Ser Leu Cys Glu Ser Thr Glu Lys Thr
```

```
                          85                  90                  95
tgc cta gac ccc ttt cga aaa ctt ctc ttc cag cta aac gac gcc agc        336
Cys Leu Asp Pro Phe Arg Lys Leu Leu Phe Gln Leu Asn Asp Ala Ser
        100                 105                 110 tct agt agc ggc ggt gct gtt cca ccg gtg agc tgt gtc gtt tcg gat        384
Ser Ser Ser Gly Gly Ala Val Pro Pro Val Ser Cys Val Val Ser Asp
            115                 120                 125 gct tct atg ccg ttc aca ctt aaa gct ggt gaa gag ttt gga ata cct        432
Ala Ser Met Pro Phe Thr Leu Lys Ala Gly Glu Glu Phe Gly Ile Pro
130                 135                 140 gtt gcg ctg ttt tgg act atc agt gct tgt ggc ttg ttg ggg tat acg        480
Val Ala Leu Phe Trp Thr Ile Ser Ala Cys Gly Leu Leu Gly Tyr Thr
145                 150                 155                 160 cag tat gag aat ctt gtc aat aaa gga ttt act ccc ttt aaa gat gag        528
Gln Tyr Glu Asn Leu Val Asn Lys Gly Phe Thr Pro Phe Lys Asp Glu
                165                 170                 175 agc tct ttt aca aat ggg tat ctg gat aca ttg ata gac tgg ata cca        576
Ser Ser Phe Thr Asn Gly Tyr Leu Asp Thr Leu Ile Asp Trp Ile Pro
                180                 185                 190 gcc gtg aat gat atc cga cta aaa gat ctt cca agc ttc ata cgc aca        624
Ala Val Asn Asp Ile Arg Leu Lys Asp Leu Pro Ser Phe Ile Arg Thr
            195                 200                 205 aca aat cca aat gat ttt atg gta aag tat gtt ata aga ttg att aaa        672
Thr Asn Pro Asn Asp Phe Met Val Lys Tyr Val Ile Arg Leu Ile Lys
210                 215                 220 cta atg tca aca gga agt gcc att atc ttt aac act ttt gac tcg tta        720
Leu Met Ser Thr Gly Ser Ala Ile Ile Phe Asn Thr Phe Asp Ser Leu
225                 230                 235                 240 gag cgc aat gtc ttg gaa gct ctt tcg tcc atg atc cca tgt cca att        768
Glu Arg Asn Val Leu Glu Ala Leu Ser Ser Met Ile Pro Cys Pro Ile
                245                 250                 255 tac aca tta ggc ccc ctc cat cta ctt gtc aac aat act caa cca aaa        816
Tyr Thr Leu Gly Pro Leu His Leu Leu Val Asn Asn Thr Gln Pro Lys
                260                 265                 270 agt ttg tcc tcc att gca tcg aat tta tgg gta gaa gag cta gaa tgc        864
Ser Leu Ser Ser Ile Ala Ser Asn Leu Trp Val Glu Glu Leu Glu Cys
            275                 280                 285 ctc caa tgg ttg gat tca aag gac tcc aaa tca att gtt tat gtc aac        912
Leu Gln Trp Leu Asp Ser Lys Asp Ser Lys Ser Ile Val Tyr Val Asn
290                 295                 300 ttt ggc agc atc act gcc gtg act ccg gaa caa ctt att gag ttc gct        960
Phe Gly Ser Ile Thr Ala Val Thr Pro Glu Gln Leu Ile Glu Phe Ala
305                 310                 315                 320 tgg ggt ttg gca aac agt aag aaa ccc ttt gtt tgg ata ata agg cca       1008
Trp Gly Leu Ala Asn Ser Lys Lys Pro Phe Val Trp Ile Ile Arg Pro
                325                 330                 335 gac ctc gtc gat gga gac tcg gcc att tta cct tca gag ttt gtg gaa       1056
Asp Leu Val Asp Gly Asp Ser Ala Ile Leu Pro Ser Glu Phe Val Glu
                340                 345                 350 gag aca agg gag aga agt ctg att tct agt tgg tgt cca caa gaa gag       1104
Glu Thr Arg Glu Arg Ser Leu Ile Ser Ser Trp Cys Pro Gln Glu Glu
            355                 360                 365 gtt ctt agc cac cct gcg att ggg ggt ttc cta acg cat tgt ggt tgg       1152
Val Leu Ser His Pro Ala Ile Gly Gly Phe Leu Thr His Cys Gly Trp
370                 375                 380 aac tcg aca ctc gaa agc ttg agc gcg gga gtg cca atg att tgt tgg       1200
Asn Ser Thr Leu Glu Ser Leu Ser Ala Gly Val Pro Met Ile Cys Trp
385                 390                 395                 400 cct ttc ttc gcc gaa caa caa act aat tgt aag ttt ttg tgc aac tat       1248
```

```
                 Pro Phe Phe Ala Glu Gln Gln Thr Asn Cys Lys Phe Leu Cys Asn Tyr
                                 405                 410                 415 tgg ggg agt gga atg gaa ata aat ccc aat gtt aag aga gat gat gtg          1296
Trp Gly Ser Gly Met Glu Ile Asn Pro Asn Val Lys Arg Asp Asp Val
                420                 425                 430 gaa aag ctt gtg agg gag ttg atg gat gga gaa aaa gga aat gat atg          1344
Glu Lys Leu Val Arg Glu Leu Met Asp Gly Glu Lys Gly Asn Asp Met
                435                 440                 445 aga aac aag gcc atg gag tgg aag cac aaa gca cat gaa gcc act gag          1392
Arg Asn Lys Ala Met Glu Trp Lys His Lys Ala His Glu Ala Thr Glu
    450                 455                 460 ctt ggt ggc tct tct ttg gtg aat ctg gat aat atc atc agt aag gtt          1440
Leu Gly Gly Ser Ser Leu Val Asn Leu Asp Asn Ile Ile Ser Lys Val
465                 470                 475                 480 ttg gtg cca tca tca aaa cca taa                                          1464
Leu Val Pro Ser Ser Lys Pro
                485

<210> SEQ ID NO 2
<211> LENGTH: 487
<212> TYPE: PRT
<213> ORGANISM: Humulus lupulus

<400> SEQUENCE: 2

Met Thr Met Glu Thr Lys Pro His Ala Val Cys Ile Pro Tyr Pro Ala
1               5                   10                  15

Gln Gly His Ile Ser Pro Met Leu Lys Leu Ala Lys Leu Leu His Gln
                20                  25                  30

Arg Gly Phe His Ile Thr Phe Val Asn Thr His Phe Asn His Asn Arg
            35                  40                  45

Leu Leu Lys Ser Arg Gly Pro Asn Ser Leu Asp Gly Leu Pro Asp Phe
    50                  55                  60

Arg Phe Glu Ser Ile Pro Asp Gly Leu Pro Pro Thr Glu Asn Lys Ala
65                  70                  75                  80

Asp Ala Thr Gln Asp Ile Pro Ser Leu Cys Glu Ser Thr Glu Lys Thr
                85                  90                  95

Cys Leu Asp Pro Phe Arg Lys Leu Leu Phe Gln Leu Asn Asp Ala Ser
                100                 105                 110

Ser Ser Ser Gly Gly Ala Val Pro Pro Val Ser Cys Val Val Ser Asp
            115                 120                 125

Ala Ser Met Pro Phe Thr Leu Lys Ala Gly Glu Glu Phe Gly Ile Pro
    130                 135                 140

Val Ala Leu Phe Trp Thr Ile Ser Ala Cys Gly Leu Leu Gly Tyr Thr
145                 150                 155                 160

Gln Tyr Glu Asn Leu Val Asn Lys Gly Phe Thr Pro Phe Lys Asp Glu
                165                 170                 175

Ser Ser Phe Thr Asn Gly Tyr Leu Asp Thr Leu Ile Asp Trp Ile Pro
            180                 185                 190

Ala Val Asn Asp Ile Arg Leu Lys Asp Leu Pro Ser Phe Ile Arg Thr
    195                 200                 205

Thr Asn Pro Asn Asp Phe Met Val Lys Tyr Val Ile Arg Leu Ile Lys
210                 215                 220

Leu Met Ser Thr Gly Ser Ala Ile Ile Phe Asn Thr Phe Asp Ser Leu
225                 230                 235                 240

Glu Arg Asn Val Leu Glu Ala Leu Ser Ser Met Ile Pro Cys Pro Ile
                245                 250                 255
```

```
Tyr Thr Leu Gly Pro Leu His Leu Leu Val Asn Asn Thr Gln Pro Lys
                260                 265                 270

Ser Leu Ser Ser Ile Ala Ser Asn Leu Trp Val Glu Glu Leu Glu Cys
            275                 280                 285

Leu Gln Trp Leu Asp Ser Lys Asp Ser Lys Ser Ile Val Tyr Val Asn
    290                 295                 300

Phe Gly Ser Ile Thr Ala Val Thr Pro Glu Gln Leu Ile Glu Phe Ala
305                 310                 315                 320

Trp Gly Leu Ala Asn Ser Lys Lys Pro Phe Val Trp Ile Ile Arg Pro
                325                 330                 335

Asp Leu Val Asp Gly Asp Ser Ala Ile Leu Pro Ser Glu Phe Val Glu
            340                 345                 350

Glu Thr Arg Glu Arg Ser Leu Ile Ser Ser Trp Cys Pro Gln Glu Glu
        355                 360                 365

Val Leu Ser His Pro Ala Ile Gly Gly Phe Leu Thr His Cys Gly Trp
    370                 375                 380

Asn Ser Thr Leu Glu Ser Leu Ser Ala Gly Val Pro Met Ile Cys Trp
385                 390                 395                 400

Pro Phe Phe Ala Glu Gln Gln Thr Asn Cys Lys Phe Leu Cys Asn Tyr
                405                 410                 415

Trp Gly Ser Gly Met Glu Ile Asn Pro Asn Val Lys Arg Asp Asp Val
            420                 425                 430

Glu Lys Leu Val Arg Glu Leu Met Asp Gly Glu Lys Gly Asn Asp Met
        435                 440                 445

Arg Asn Lys Ala Met Glu Trp Lys His Lys Ala His Glu Ala Thr Glu
    450                 455                 460

Leu Gly Gly Ser Ser Leu Val Asn Leu Asp Asn Ile Ile Ser Lys Val
465                 470                 475                 480

Leu Val Pro Ser Ser Lys Pro
                485

<210> SEQ ID NO 3
<211> LENGTH: 1464
<212> TYPE: DNA
<213> ORGANISM: Humulus lupulus
<220> FEATURE:
<221> NAME/KEY: CDS
<222> LOCATION: (1)..(1461)

<400> SEQUENCE: 3 atg acc atg gaa act aag cct cac gca gta tgc atc cca tac cca gca    48
Met Thr Met Glu Thr Lys Pro His Ala Val Cys Ile Pro Tyr Pro Ala
1               5                   10                  15 cag ggc cat ata aac cct atg ctg aaa ctg gcc aag ctt ctc cac cag    96
Gln Gly His Ile Asn Pro Met Leu Lys Leu Ala Lys Leu Leu His Gln
            20                  25                  30 aga ggc ttc cac ata acc ttc gtc aac acc cac ttc aac cac aac cgt   144
Arg Gly Phe His Ile Thr Phe Val Asn Thr His Phe Asn His Asn Arg
        35                  40                  45 ctc ctc aaa tct aga ggc ccc aac tcc ctc gat ggc ttg ccc gat ttt   192
Leu Leu Lys Ser Arg Gly Pro Asn Ser Leu Asp Gly Leu Pro Asp Phe
    50                  55                  60 cgc ttc gaa tca atc ccg gac ggc ctt cct ccg acg gag aac aaa gcc   240
Arg Phe Glu Ser Ile Pro Asp Gly Leu Pro Pro Thr Glu Asn Lys Ala
65                  70                  75                  80 gac gcc acg cag gac atc cca tcc ctg tgc gag tcc acc gaa aag acc   288
Asp Ala Thr Gln Asp Ile Pro Ser Leu Cys Glu Ser Thr Glu Lys Thr
                85                  90                  95
```

-continued

| | | |
|---|---|---|
| tgc cta gac ccc ttt cga aaa ctt ctc ttc cag cta aac gac gcc agc<br>Cys Leu Asp Pro Phe Arg Lys Leu Leu Phe Gln Leu Asn Asp Ala Ser<br>            100                        105                  110 | | 336 |
| tct agt agc ggc ggt gct gtt cca ccg gtg agc tgt gtc gtt tcg gat<br>Ser Ser Ser Gly Gly Ala Val Pro Pro Val Ser Cys Val Val Ser Asp<br>        115                      120                  125 | | 384 |
| cct gct atg ccg ttc aca ctt aca gct ggt gaa gag ttt gga ata cct<br>Pro Ala Met Pro Phe Thr Leu Thr Ala Gly Glu Glu Phe Gly Ile Pro<br>130                      135                  140 | | 432 |
| gtt gcg ctg ttt tgg act atc agt gct tgt ggc ttg ttg ggg tat acg<br>Val Ala Leu Phe Trp Thr Ile Ser Ala Cys Gly Leu Leu Gly Tyr Thr<br>145                  150                  155                  160 | | 480 |
| cag tat gag aat ctt gtc aac aaa ggg ttt act ccc ttt aaa gat gag<br>Gln Tyr Glu Asn Leu Val Asn Lys Gly Phe Thr Pro Phe Lys Asp Glu<br>                  165                  170                  175 | | 528 |
| agc tct ttt aca aat ggg tat ctg gat aca ttg ata gac tgg ata cca<br>Ser Ser Phe Thr Asn Gly Tyr Leu Asp Thr Leu Ile Asp Trp Ile Pro<br>        180                      185                  190 | | 576 |
| gcc gtg aat gat atc cga cta aaa gat ctt cca agc ttc ata cgc aca<br>Ala Val Asn Asp Ile Arg Leu Lys Asp Leu Pro Ser Phe Ile Arg Thr<br>195                      200                  205 | | 624 |
| aca aat cca aat gaa ttt atg gta aag tat gtt ata aga ttg att aaa<br>Thr Asn Pro Asn Glu Phe Met Val Lys Tyr Val Ile Arg Leu Ile Lys<br>210                      215                  220 | | 672 |
| cta act tca aca gga aat gcc atg atc ttt aac act ttt gac tcg tta<br>Leu Thr Ser Thr Gly Asn Ala Met Ile Phe Asn Thr Phe Asp Ser Leu<br>225                  230                  235                  240 | | 720 |
| gag cac aat gtc ttg gaa gct ctt tcg tcc atg ttc cca tgt cca att<br>Glu His Asn Val Leu Glu Ala Leu Ser Ser Met Phe Pro Cys Pro Ile<br>                  245                  250                  255 | | 768 |
| tac aca tta ggc ccc ctc cat gta ctt gtc aac aag act caa tca aaa<br>Tyr Thr Leu Gly Pro Leu His Val Leu Val Asn Lys Thr Gln Ser Lys<br>        260                      265                  270 | | 816 |
| agt ttg tcc tcc att gca tcg aat tta tgg gta gaa gag cta gaa tgc<br>Ser Leu Ser Ser Ile Ala Ser Asn Leu Trp Val Glu Glu Leu Glu Cys<br>275                  280                  285 | | 864 |
| ctc caa tgg ttg gat tca aag gat tcc aaa tca att gtt tat gtc aac<br>Leu Gln Trp Leu Asp Ser Lys Asp Ser Lys Ser Ile Val Tyr Val Asn<br>        290                      295                  300 | | 912 |
| ttt ggc agc atc act gcc gtg act ccg gaa caa ctt gtt gag ttc gct<br>Phe Gly Ser Ile Thr Ala Val Thr Pro Glu Gln Leu Val Glu Phe Ala<br>305                  310                  315                  320 | | 960 |
| tgg ggt ttg gca aac agt aag aaa ccc ttt gtt tgg ata ata agg cca<br>Trp Gly Leu Ala Asn Ser Lys Lys Pro Phe Val Trp Ile Ile Arg Pro<br>                  325                  330                  335 | | 1008 |
| gac ctc gtc gat gga gac tcg gcc att tta cct tcg gag ttt gtg gaa<br>Asp Leu Val Asp Gly Asp Ser Ala Ile Leu Pro Ser Glu Phe Val Glu<br>                  340                  345                  350 | | 1056 |
| gag aca agg gag aga agt ctg att tct agt tgg tgt cca caa gaa gag<br>Glu Thr Arg Glu Arg Ser Leu Ile Ser Ser Trp Cys Pro Gln Glu Glu<br>                  355                  360                  365 | | 1104 |
| gtt ctt agc cac cct gcg att ggg ggt ttc cta acg cat tgt ggt tgg<br>Val Leu Ser His Pro Ala Ile Gly Gly Phe Leu Thr His Cys Gly Trp<br>370                      375                  380 | | 1152 |
| aac tcg aca ctt gaa agc ttg agc gcg gga gtg cca acg att tgt tgg<br>Asn Ser Thr Leu Glu Ser Leu Ser Ala Gly Val Pro Thr Ile Cys Trp<br>385                  390                  395                  400 | | 1200 |
| cct ttc ttc gcc gag caa caa act aat tgt aag ttt ttg tgc gac tat<br>Pro Phe Phe Ala Glu Gln Gln Thr Asn Cys Lys Phe Leu Cys Asp Tyr | | 1248 |

```
                405                 410                 415
tgg ggg agt gga atg gaa ata aat ccc aat gtt aag aga gat gat gtt      1296
Trp Gly Ser Gly Met Glu Ile Asn Pro Asn Val Lys Arg Asp Asp Val
            420                 425                 430 gaa aag ctt gtg agg gag ttg atg gat gga gaa aaa gga aat gat atg      1344
Glu Lys Leu Val Arg Glu Leu Met Asp Gly Glu Lys Gly Asn Asp Met
        435                 440                 445 aga aac aag gcc atg gag tgg aag cac aaa gca cat gaa gcc acc gag      1392
Arg Asn Lys Ala Met Glu Trp Lys His Lys Ala His Glu Ala Thr Glu
450                 455                 460 ctt ggt ggc tct tct ttg gtg aat ctg gat aat atc atc agt aag gtg      1440
Leu Gly Gly Ser Ser Leu Val Asn Leu Asp Asn Ile Ile Ser Lys Val
465                 470                 475                 480 ttg gtg cca tca tca aaa cca taa                                      1464
Leu Val Pro Ser Ser Lys Pro
                485
```

<210> SEQ ID NO 4
<211> LENGTH: 487
<212> TYPE: PRT
<213> ORGANISM: Humulus lupulus

<400> SEQUENCE: 4

```
Met Thr Met Glu Thr Lys Pro His Ala Val Cys Ile Pro Tyr Pro Ala
1               5                   10                  15

Gln Gly His Ile Asn Pro Met Leu Lys Leu Ala Lys Leu Leu His Gln
                20                  25                  30

Arg Gly Phe His Ile Thr Phe Val Asn Thr His Phe Asn His Asn Arg
            35                  40                  45

Leu Leu Lys Ser Arg Gly Pro Asn Ser Leu Asp Gly Leu Pro Asp Phe
50                  55                  60

Arg Phe Glu Ser Ile Pro Asp Gly Leu Pro Pro Thr Glu Asn Lys Ala
65                  70                  75                  80

Asp Ala Thr Gln Asp Ile Pro Ser Leu Cys Glu Ser Thr Glu Lys Thr
                85                  90                  95

Cys Leu Asp Pro Phe Arg Lys Leu Leu Phe Gln Leu Asn Asp Ala Ser
            100                 105                 110

Ser Ser Ser Gly Gly Ala Val Pro Val Ser Cys Val Val Ser Asp
        115                 120                 125

Pro Ala Met Pro Phe Thr Leu Thr Ala Gly Glu Glu Phe Gly Ile Pro
130                 135                 140

Val Ala Leu Phe Trp Thr Ile Ser Ala Cys Gly Leu Leu Gly Tyr Thr
145                 150                 155                 160

Gln Tyr Glu Asn Leu Val Asn Lys Gly Phe Thr Pro Phe Lys Asp Glu
                165                 170                 175

Ser Ser Phe Thr Asn Gly Tyr Leu Asp Thr Leu Ile Asp Trp Ile Pro
            180                 185                 190

Ala Val Asn Asp Ile Arg Leu Lys Asp Leu Pro Ser Phe Ile Arg Thr
        195                 200                 205

Thr Asn Pro Asn Glu Phe Met Val Lys Tyr Val Ile Arg Leu Ile Lys
210                 215                 220

Leu Thr Ser Thr Gly Asn Ala Met Ile Phe Asn Thr Phe Asp Ser Leu
225                 230                 235                 240

Glu His Asn Val Leu Glu Ala Leu Ser Ser Met Phe Pro Cys Pro Ile
                245                 250                 255

Tyr Thr Leu Gly Pro Leu His Val Leu Val Asn Lys Thr Gln Ser Lys
```

```
                260                 265                 270
Ser Leu Ser Ser Ile Ala Ser Asn Leu Trp Val Glu Glu Leu Glu Cys
            275                 280                 285

Leu Gln Trp Leu Asp Ser Lys Asp Ser Lys Ser Ile Val Tyr Val Asn
        290                 295                 300

Phe Gly Ser Ile Thr Ala Val Thr Pro Glu Gln Leu Val Glu Phe Ala
305                 310                 315                 320

Trp Gly Leu Ala Asn Ser Lys Lys Pro Phe Val Trp Ile Ile Arg Pro
                325                 330                 335

Asp Leu Val Asp Gly Asp Ser Ala Ile Leu Pro Ser Glu Phe Val Glu
            340                 345                 350

Glu Thr Arg Glu Arg Ser Leu Ile Ser Ser Trp Cys Pro Gln Glu Glu
        355                 360                 365

Val Leu Ser His Pro Ala Ile Gly Gly Phe Leu Thr His Cys Gly Trp
            370                 375                 380

Asn Ser Thr Leu Glu Ser Leu Ser Ala Gly Val Pro Thr Ile Cys Trp
385                 390                 395                 400

Pro Phe Phe Ala Glu Gln Gln Thr Asn Cys Lys Phe Leu Cys Asp Tyr
                405                 410                 415

Trp Gly Ser Gly Met Glu Ile Asn Pro Asn Val Lys Arg Asp Asp Val
            420                 425                 430

Glu Lys Leu Val Arg Glu Leu Met Asp Gly Lys Gly Asn Asp Met
        435                 440                 445

Arg Asn Lys Ala Met Glu Trp Lys His Lys Ala His Glu Ala Thr Glu
    450                 455                 460

Leu Gly Gly Ser Ser Leu Val Asn Leu Asp Asn Ile Ile Ser Lys Val
465                 470                 475                 480

Leu Val Pro Ser Ser Lys Pro
                485

<210> SEQ ID NO 5
<211> LENGTH: 1464
<212> TYPE: DNA
<213> ORGANISM: Humulus lupulus
<220> FEATURE:
<221> NAME/KEY: CDS
<222> LOCATION: (1)..(1461)

<400> SEQUENCE: 5 atg acc atg gaa act aag cct cac gca gta tgc atc cca tac cca gca      48
Met Thr Met Glu Thr Lys Pro His Ala Val Cys Ile Pro Tyr Pro Ala
1               5                   10                  15 cag ggc cat ata aac cct atg ctg aaa ctg gcc aag ctt ctc cac cag      96
Gln Gly His Ile Asn Pro Met Leu Lys Leu Ala Lys Leu Leu His Gln
            20                  25                  30 aga ggc ttc cac ata acc ttc gtc aac acc cac ttc aac cac aac cgt     144
Arg Gly Phe His Ile Thr Phe Val Asn Thr His Phe Asn His Asn Arg
        35                  40                  45 atc ctc aaa tct aga ggc ccc aac tcc ctc gac ggc ttg ccc gat ttt     192
Ile Leu Lys Ser Arg Gly Pro Asn Ser Leu Asp Gly Leu Pro Asp Phe
    50                  55                  60 cgc ttc gaa tca atc ccg gac ggc ctt cct ccg acg gag aac aaa gcc     240
Arg Phe Glu Ser Ile Pro Asp Gly Leu Pro Pro Thr Glu Asn Lys Ala
65                  70                  75                  80 gac gcc acg cag gac atc cca tcc ctg tgc gag tcc acc gaa aag acc     288
Asp Ala Thr Gln Asp Ile Pro Ser Leu Cys Glu Ser Thr Glu Lys Thr
                85                  90                  95
```

| | | |
|---|---|---|
| tgc cta gac ccc ttt cga aaa ctt ctc ttc cag cta aac gac gcc agc<br>Cys Leu Asp Pro Phe Arg Lys Leu Leu Phe Gln Leu Asn Asp Ala Ser<br>100              105                  110 | | 336 |
| tct agt agc ggc ggt gct gtt cca ccg gtg agc tgt gtc gtt tcg gat<br>Ser Ser Ser Gly Gly Ala Val Pro Pro Val Ser Cys Val Val Ser Asp<br>    115                  120                  125 | | 384 |
| gct gct atg ccg ttc acc ctt aaa gct ggt gaa gag ttt gga ata cca<br>Ala Ala Met Pro Phe Thr Leu Lys Ala Gly Glu Glu Phe Gly Ile Pro<br>130              135                  140 | | 432 |
| gtt gcg ctg ttt tgg act atc agt gct tgc ggc ttg ttg ggg tat acg<br>Val Ala Leu Phe Trp Thr Ile Ser Ala Cys Gly Leu Leu Gly Tyr Thr<br>145                  150                  155                  160 | | 480 |
| cag tat gag aat ctt gtc aat aaa gga ttt act ccc ttt aaa gat gag<br>Gln Tyr Glu Asn Leu Val Asn Lys Gly Phe Thr Pro Phe Lys Asp Glu<br>        165                  170                  175 | | 528 |
| agc tct ttt aca aat ggg tat ctg gat aca ttg ata gat tgg ata cca<br>Ser Ser Phe Thr Asn Gly Tyr Leu Asp Thr Leu Ile Asp Trp Ile Pro<br>    180                  185                  190 | | 576 |
| gtc gtg aat gat atc cga cta aaa gat ctt cca agc ttc ata cgc aca<br>Val Val Asn Asp Ile Arg Leu Lys Asp Leu Pro Ser Phe Ile Arg Thr<br>195                  200                  205 | | 624 |
| aca aat cca aat gaa ttt atg gta aag tat gtt ata aga ttg att aaa<br>Thr Asn Pro Asn Glu Phe Met Val Lys Tyr Val Ile Arg Leu Ile Lys<br>210                  215                  220 | | 672 |
| cta act tca aca ggg agt gcc att atc ttt aac act ttt gac gca tta<br>Leu Thr Ser Thr Gly Ser Ala Ile Ile Phe Asn Thr Phe Asp Ala Leu<br>225                  230                  235                  240 | | 720 |
| gag cac aat gtc ttg gaa gct ctt tcg tcc atg ttc cca tgt cca att<br>Glu His Asn Val Leu Glu Ala Leu Ser Ser Met Phe Pro Cys Pro Ile<br>        245                  250                  255 | | 768 |
| tac aca tta ggt ccc ctc cat cta ctt gtc aac aag act caa cca aaa<br>Tyr Thr Leu Gly Pro Leu His Leu Leu Val Asn Lys Thr Gln Pro Lys<br>    260                  265                  270 | | 816 |
| agt ctg tcc tcc att gca tcg aat tta tgg gta gaa gag cta gaa tgc<br>Ser Leu Ser Ser Ile Ala Ser Asn Leu Trp Val Glu Glu Leu Glu Cys<br>275                  280                  285 | | 864 |
| ctc caa tgg ttg gat tca aag gac tcc aaa tca att gtt tat gtc aac<br>Leu Gln Trp Leu Asp Ser Lys Asp Ser Lys Ser Ile Val Tyr Val Asn<br>290                  295                  300 | | 912 |
| ttt ggc agc atc act gcc gtg act ccg gaa caa ctt att gag ttc gct<br>Phe Gly Ser Ile Thr Ala Val Thr Pro Glu Gln Leu Ile Glu Phe Ala<br>305                  310                  315                  320 | | 960 |
| tgg ggt ttg gca aac agt aag aaa ccc ttt gtt tgg ata ata agg cca<br>Trp Gly Leu Ala Asn Ser Lys Lys Pro Phe Val Trp Ile Ile Arg Pro<br>        325                  330                  335 | | 1008 |
| gac ctc gtc gat gga gac tcg gcc att tta cct tca gag ttt gtg gaa<br>Asp Leu Val Asp Gly Asp Ser Ala Ile Leu Pro Ser Glu Phe Val Glu<br>    340                  345                  350 | | 1056 |
| gag aca agg gag aga agt ctg att tct agt tgg tgt cca caa gaa gag<br>Glu Thr Arg Glu Arg Ser Leu Ile Ser Ser Trp Cys Pro Gln Glu Glu<br>355                  360                  365 | | 1104 |
| gtt ctt agc cac cct gcg att ggg ggt ttc cta acg cat tgt ggt tgg<br>Val Leu Ser His Pro Ala Ile Gly Gly Phe Leu Thr His Cys Gly Trp<br>370                  375                  380 | | 1152 |
| aac tcg aca ctc gaa agc ttg agc gct gga gtg cca atg att tgt tgg<br>Asn Ser Thr Leu Glu Ser Leu Ser Ala Gly Val Pro Met Ile Cys Trp<br>385                  390                  395                  400 | | 1200 |
| ccc ttc ttt gcc gag caa caa act aat tgt aag ttt ttg tgc gac tat<br>Pro Phe Phe Ala Glu Gln Gln Thr Asn Cys Lys Phe Leu Cys Asp Tyr<br>        405                  410                  415 | | 1248 |

```
tgg ggg agt gga atg gaa ata aat ccc aat gtt aag aga gat gat gtg      1296
Trp Gly Ser Gly Met Glu Ile Asn Pro Asn Val Lys Arg Asp Asp Val
            420                 425                 430 gaa aag ctt gtg agg gaa ttg atg gat gga gaa aaa gga aat gat atg      1344
Glu Lys Leu Val Arg Glu Leu Met Asp Gly Glu Lys Gly Asn Asp Met
        435                 440                 445 aga aac aag gcc atg gag tgg aag cac aaa gca cat gaa gcc acc gag      1392
Arg Asn Lys Ala Met Glu Trp Lys His Lys Ala His Glu Ala Thr Glu
450                 455                 460 ctt ggt ggc tct tct ttg gtg aat ctg gat aat atc atc agt aag gtt      1440
Leu Gly Gly Ser Ser Leu Val Asn Leu Asp Asn Ile Ile Ser Lys Val
465                 470                 475                 480 ttg gtg cca tca tca aaa cca taa                                      1464
Leu Val Pro Ser Ser Lys Pro
                485

<210> SEQ ID NO 6
<211> LENGTH: 487
<212> TYPE: PRT
<213> ORGANISM: Humulus lupulus

<400> SEQUENCE: 6

Met Thr Met Glu Thr Lys Pro His Ala Val Cys Ile Pro Tyr Pro Ala
1               5                   10                  15

Gln Gly His Ile Asn Pro Met Leu Lys Leu Ala Lys Leu Leu His Gln
            20                  25                  30

Arg Gly Phe His Ile Thr Phe Val Asn Thr His Phe Asn His Asn Arg
        35                  40                  45

Ile Leu Lys Ser Arg Gly Pro Asn Ser Leu Asp Gly Leu Pro Asp Phe
    50                  55                  60

Arg Phe Glu Ser Ile Pro Asp Gly Leu Pro Pro Thr Glu Asn Lys Ala
65                  70                  75                  80

Asp Ala Thr Gln Asp Ile Pro Ser Leu Cys Glu Ser Thr Glu Lys Thr
                85                  90                  95

Cys Leu Asp Pro Phe Arg Lys Leu Leu Phe Gln Leu Asn Asp Ala Ser
            100                 105                 110

Ser Ser Ser Gly Gly Ala Val Pro Val Ser Cys Val Val Ser Asp
        115                 120                 125

Ala Ala Met Pro Phe Thr Leu Lys Ala Gly Glu Glu Phe Gly Ile Pro
    130                 135                 140

Val Ala Leu Phe Trp Thr Ile Ser Ala Cys Gly Leu Leu Gly Tyr Thr
145                 150                 155                 160

Gln Tyr Glu Asn Leu Val Asn Lys Gly Phe Thr Pro Phe Lys Asp Glu
                165                 170                 175

Ser Ser Phe Thr Asn Gly Tyr Leu Asp Thr Leu Ile Asp Trp Ile Pro
            180                 185                 190

Val Val Asn Asp Ile Arg Leu Lys Asp Leu Pro Ser Phe Ile Arg Thr
        195                 200                 205

Thr Asn Pro Asn Glu Phe Met Val Lys Tyr Val Ile Arg Leu Ile Lys
    210                 215                 220

Leu Thr Ser Thr Gly Ser Ala Ile Ile Phe Asn Thr Phe Asp Ala Leu
225                 230                 235                 240

Glu His Asn Val Leu Glu Ala Leu Ser Ser Met Phe Pro Cys Pro Ile
                245                 250                 255

Tyr Thr Leu Gly Pro Leu His Leu Leu Val Asn Lys Thr Gln Pro Lys
            260                 265                 270
```

```
Ser Leu Ser Ser Ile Ala Ser Asn Leu Trp Val Glu Leu Glu Cys
        275                 280                 285

Leu Gln Trp Leu Asp Ser Lys Asp Ser Lys Ser Ile Val Tyr Val Asn
290                 295                 300

Phe Gly Ser Ile Thr Ala Val Thr Pro Glu Gln Leu Ile Glu Phe Ala
305                 310                 315                 320

Trp Gly Leu Ala Asn Ser Lys Lys Pro Phe Val Trp Ile Ile Arg Pro
                325                 330                 335

Asp Leu Val Asp Gly Asp Ser Ala Ile Leu Pro Ser Glu Phe Val Glu
                340                 345                 350

Glu Thr Arg Glu Arg Ser Leu Ile Ser Ser Trp Cys Pro Gln Glu Glu
            355                 360                 365

Val Leu Ser His Pro Ala Ile Gly Gly Phe Leu Thr His Cys Gly Trp
        370                 375                 380

Asn Ser Thr Leu Glu Ser Leu Ser Ala Gly Val Pro Met Ile Cys Trp
385                 390                 395                 400

Pro Phe Phe Ala Glu Gln Gln Thr Asn Cys Lys Phe Leu Cys Asp Tyr
                405                 410                 415

Trp Gly Ser Gly Met Glu Ile Asn Pro Asn Val Lys Arg Asp Asp Val
                420                 425                 430

Glu Lys Leu Val Arg Glu Leu Met Asp Gly Glu Lys Gly Asn Asp Met
            435                 440                 445

Arg Asn Lys Ala Met Glu Trp Lys His Lys Ala His Glu Ala Thr Glu
        450                 455                 460

Leu Gly Gly Ser Ser Leu Val Asn Leu Asp Asn Ile Ile Ser Lys Val
465                 470                 475                 480

Leu Val Pro Ser Ser Lys Pro
                485

<210> SEQ ID NO 7
<211> LENGTH: 1455
<212> TYPE: DNA
<213> ORGANISM: Humulus lupulus
<220> FEATURE:
<221> NAME/KEY: CDS
<222> LOCATION: (1)..(1452)

<400> SEQUENCE: 7 atg ggt tca atc agc gaa atg atg aag ccg cat gca gtg tgt gtt cca      48
Met Gly Ser Ile Ser Glu Met Met Lys Pro His Ala Val Cys Val Pro
1               5                   10                  15 ttt cca gca caa gga cat gtt aac ccc atg atg caa cta gcc aag ctt      96
Phe Pro Ala Gln Gly His Val Asn Pro Met Met Gln Leu Ala Lys Leu
                20                  25                  30 cta cac tca aga ggc ttc cat ata act tat gtc aac act gag ttc aac     144
Leu His Ser Arg Gly Phe His Ile Thr Tyr Val Asn Thr Glu Phe Asn
            35                  40                  45 cac agg cgc tta atc aga tcg aga ggt ccg gac tct gtg aaa ggc cta     192
His Arg Arg Leu Ile Arg Ser Arg Gly Pro Asp Ser Val Lys Gly Leu
        50                  55                  60 cct gac ttt cag ttt gag acc ata cca gat ggt ttg cca cca tca gat     240
Pro Asp Phe Gln Phe Glu Thr Ile Pro Asp Gly Leu Pro Pro Ser Asp
65                  70                  75                  80 cgt gat gca acc caa gaa gtt cca cct tta tgt gac gca act aga aag     288
Arg Asp Ala Thr Gln Glu Val Pro Pro Leu Cys Asp Ala Thr Arg Lys
                85                  90                  95 aac tgt tta ggt cca ttt aaa gag ctt tta cat aag ctc aga agt tgt     336
```

-continued

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Asn | Cys | Leu | Gly | Pro | Phe | Lys | Glu | Leu | Leu | His | Lys | Leu | Arg | Ser | Cys |     |
|     |     |     | 100 |     |     |     | 105 |     |     |     | 110 |     |     |     |     |     |

| tct | gaa | gtg | cct | cca | gtc | act | tgc | atc | att | act | gat | ggg | atc | atg | acc | 384 |
|-----|-----|-----|-----|-----|-----|-----|-----|-----|-----|-----|-----|-----|-----|-----|-----|-----|
| Ser | Glu | Val | Pro | Pro | Val | Thr | Cys | Ile | Ile | Thr | Asp | Gly | Ile | Met | Thr |     |
|     |     | 115 |     |     |     |     | 120 |     |     |     |     | 125 |     |     |     |     |

| ttt | ggt | ata | aaa | gct | gct | agg | gag | ttt | ggg | att | cca | gag | gtt | gtt | ttt | 432 |
| Phe | Gly | Ile | Lys | Ala | Ala | Arg | Glu | Phe | Gly | Ile | Pro | Glu | Val | Val | Phe |     |
|     | 130 |     |     |     |     | 135 |     |     |     |     | 140 |     |     |     |     |     |

| tgg | act | gct | tct | gct | tgt | agc | ttc | atg | ggg | tac | ctc | caa | tac | gat | gaa | 480 |
| Trp | Thr | Ala | Ser | Ala | Cys | Ser | Phe | Met | Gly | Tyr | Leu | Gln | Tyr | Asp | Glu |     |
| 145 |     |     |     |     | 150 |     |     |     |     | 155 |     |     |     |     | 160 |     |

| ctt | gtc | aga | aga | ggc | atc | gtt | cct | ttc | aaa | gac | gaa | agc | ttc | atg | cta | 528 |
| Leu | Val | Arg | Arg | Gly | Ile | Val | Pro | Phe | Lys | Asp | Glu | Ser | Phe | Met | Leu |     |
|     |     |     |     | 165 |     |     |     |     | 170 |     |     |     |     | 175 |     |     |

| gat | ggt | act | ctt | gac | aca | cca | ata | gac | tgg | att | cca | ggc | ata | aga | gat | 576 |
| Asp | Gly | Thr | Leu | Asp | Thr | Pro | Ile | Asp | Trp | Ile | Pro | Gly | Ile | Arg | Asp |     |
|     |     |     | 180 |     |     |     |     | 185 |     |     |     |     | 190 |     |     |     |

| gta | aga | ctg | agg | gac | ttg | cca | agc | ttc | ttg | aga | gtg | aca | tca | acc | gac | 624 |
| Val | Arg | Leu | Arg | Asp | Leu | Pro | Ser | Phe | Leu | Arg | Val | Thr | Ser | Thr | Asp |     |
|     |     | 195 |     |     |     |     | 200 |     |     |     |     | 205 |     |     |     |     |

| gac | ata | atg | ttc | gat | ttt | ctc | gga | tca | caa | gca | aag | aac | tgc | ctg | act | 672 |
| Asp | Ile | Met | Phe | Asp | Phe | Leu | Gly | Ser | Gln | Ala | Lys | Asn | Cys | Leu | Thr |     |
| 210 |     |     |     |     | 215 |     |     |     |     | 220 |     |     |     |     |     |     |

| tct | tcc | gct | ata | atc | ttc | aac | aca | ttc | cga | gag | cta | gag | cta | gaa | gta | 720 |
| Ser | Ser | Ala | Ile | Ile | Phe | Asn | Thr | Phe | Arg | Glu | Leu | Glu | Leu | Glu | Val |     |
| 225 |     |     |     |     | 230 |     |     |     |     | 235 |     |     |     |     | 240 |     |

| cta | gat | tcg | atc | tcg | gac | atg | tac | cca | aac | atc | tac | act | ata | gga | cca | 768 |
| Leu | Asp | Ser | Ile | Ser | Asp | Met | Tyr | Pro | Asn | Ile | Tyr | Thr | Ile | Gly | Pro |     |
|     |     |     |     | 245 |     |     |     |     | 250 |     |     |     |     | 255 |     |     |

| ctt | cct | atg | ctc | aac | cgt | cat | ctt | cca | gct | gaa | agt | caa | gtc | aag | tcc | 816 |
| Leu | Pro | Met | Leu | Asn | Arg | His | Leu | Pro | Ala | Glu | Ser | Gln | Val | Lys | Ser |     |
|     |     |     | 260 |     |     |     |     | 265 |     |     |     |     | 270 |     |     |     |

| atg | agt | aca | agc | tta | tgg | aaa | gaa | gac | tca | aca | tgt | ttc | caa | tgg | ctc | 864 |
| Met | Ser | Thr | Ser | Leu | Trp | Lys | Glu | Asp | Ser | Thr | Cys | Phe | Gln | Trp | Leu |     |
|     |     | 275 |     |     |     |     | 280 |     |     |     |     | 285 |     |     |     |     |

| cac | aaa | aga | gaa | ccc | aat | tca | gtt | gtg | tac | gtg | aac | tat | gga | agc | atc | 912 |
| His | Lys | Arg | Glu | Pro | Asn | Ser | Val | Val | Tyr | Val | Asn | Tyr | Gly | Ser | Ile |     |
|     | 290 |     |     |     |     | 295 |     |     |     |     | 300 |     |     |     |     |     |

| aca | aca | atg | act | gaa | gac | aat | ttc | aga | gaa | ttt | gct | tgg | gga | ctt | gct | 960 |
| Thr | Thr | Met | Thr | Glu | Asp | Asn | Phe | Arg | Glu | Phe | Ala | Trp | Gly | Leu | Ala |     |
| 305 |     |     |     |     | 310 |     |     |     |     | 315 |     |     |     |     | 320 |     |

| aat | agt | aaa | cac | tcg | ttt | gtg | tgg | ata | gtt | agg | cct | gat | gtt | ata | atg | 1008 |
| Asn | Ser | Lys | His | Ser | Phe | Val | Trp | Ile | Val | Arg | Pro | Asp | Val | Ile | Met |      |
|     |     |     |     | 325 |     |     |     |     | 330 |     |     |     |     | 335 |     |      |

| ggt | tct | aat | tca | gcc | act | gtt | ttg | ccc | gaa | gaa | ttt | ttc | gag | gag | att | 1056 |
| Gly | Ser | Asn | Ser | Ala | Thr | Val | Leu | Pro | Glu | Glu | Phe | Phe | Glu | Glu | Ile |      |
|     |     |     | 340 |     |     |     |     | 345 |     |     |     |     | 350 |     |     |      |

| aag | gat | aga | ggg | ctg | ctg | gca | aac | tgg | tgc | caa | caa | aag | gaa | gtt | ttg | 1104 |
| Lys | Asp | Arg | Gly | Leu | Leu | Ala | Asn | Trp | Cys | Gln | Gln | Lys | Glu | Val | Leu |      |
|     |     | 355 |     |     |     |     | 360 |     |     |     |     | 365 |     |     |     |      |

| gaa | cat | tct | tca | gtt | ggg | gtt | ttc | tta | acc | cat | tgt | ggt | tgg | aac | tcc | 1152 |
| Glu | His | Ser | Ser | Val | Gly | Val | Phe | Leu | Thr | His | Cys | Gly | Trp | Asn | Ser |      |
|     | 370 |     |     |     |     | 375 |     |     |     |     | 380 |     |     |     |     |      |

| act | gtg | gag | act | gtg | tgt | gct | ggt | gtg | cct | gtg | att | tgc | tgg | cct | ttc | 1200 |
| Thr | Val | Glu | Thr | Val | Cys | Ala | Gly | Val | Pro | Val | Ile | Cys | Trp | Pro | Phe |      |
| 385 |     |     |     |     | 390 |     |     |     |     | 395 |     |     |     |     | 400 |      |

| ttt | gct | gat | cag | caa | acc | aac | tgt | cat | ttt | gct | tgt | aaa | aca | ttg | ggt | 1248 |
| Phe | Ala | Asp | Gln | Gln | Thr | Asn | Cys | His | Phe | Ala | Cys | Lys | Thr | Leu | Gly |      |
|     |     |     |     | 405 |     |     |     |     | 410 |     |     |     |     | 415 |     |      |

```
att ggg gtg gaa att agc cct gat gtc aaa aga gag gaa gtc act ggg      1296
Ile Gly Val Glu Ile Ser Pro Asp Val Lys Arg Glu Glu Val Thr Gly
            420                 425                 430 ctt gtg aag gag atg atg gaa ggg gag aag ggg gag aaa atg agg gaa      1344
Leu Val Lys Glu Met Met Glu Gly Glu Lys Gly Glu Lys Met Arg Glu
        435                 440                 445 aag gct tcg tat tgg aag aag aaa gca gct gaa act act gac att ggt      1392
Lys Ala Ser Tyr Trp Lys Lys Lys Ala Ala Glu Thr Thr Asp Ile Gly
    450                 455                 460 ggt gat tct tat cat gat ttt gac aaa ttg att aag agt ctc ggc ttt      1440
Gly Asp Ser Tyr His Asp Phe Asp Lys Leu Ile Lys Ser Leu Gly Phe
465                 470                 475                 480 gat ggt agg gac taa                                                   1455
Asp Gly Arg Asp <210> SEQ ID NO 8
<211> LENGTH: 484
<212> TYPE: PRT
<213> ORGANISM: Humulus lupulus

<400> SEQUENCE: 8

Met Gly Ser Ile Ser Glu Met Met Lys Pro His Ala Val Cys Val Pro
1               5                   10                  15

Phe Pro Ala Gln Gly His Val Asn Pro Met Met Gln Leu Ala Lys Leu
            20                  25                  30

Leu His Ser Arg Gly Phe His Ile Thr Tyr Val Asn Thr Glu Phe Asn
        35                  40                  45

His Arg Arg Leu Ile Arg Ser Arg Gly Pro Asp Ser Val Lys Gly Leu
    50                  55                  60

Pro Asp Phe Gln Phe Glu Thr Ile Pro Asp Gly Leu Pro Pro Ser Asp
65                  70                  75                  80

Arg Asp Ala Thr Gln Glu Val Pro Pro Leu Cys Asp Ala Thr Arg Lys
                85                  90                  95

Asn Cys Leu Gly Pro Phe Lys Glu Leu Leu His Lys Leu Arg Ser Cys
            100                 105                 110

Ser Glu Val Pro Pro Val Thr Cys Ile Ile Thr Asp Gly Ile Met Thr
        115                 120                 125

Phe Gly Ile Lys Ala Ala Arg Glu Phe Gly Ile Pro Glu Val Val Phe
    130                 135                 140

Trp Thr Ala Ser Ala Cys Ser Phe Met Gly Tyr Leu Gln Tyr Asp Glu
145                 150                 155                 160

Leu Val Arg Arg Gly Ile Val Pro Phe Lys Asp Glu Ser Phe Met Leu
                165                 170                 175

Asp Gly Thr Leu Asp Thr Pro Ile Asp Trp Ile Pro Gly Ile Arg Asp
            180                 185                 190

Val Arg Leu Arg Asp Leu Pro Ser Phe Leu Arg Val Thr Ser Thr Asp
        195                 200                 205

Asp Ile Met Phe Asp Phe Leu Gly Ser Gln Ala Lys Asn Cys Leu Thr
    210                 215                 220

Ser Ser Ala Ile Ile Phe Asn Thr Phe Arg Glu Leu Glu Leu Glu Val
225                 230                 235                 240

Leu Asp Ser Ile Ser Asp Met Tyr Pro Asn Ile Tyr Thr Ile Gly Pro
                245                 250                 255

Leu Pro Met Leu Asn Arg His Leu Pro Ala Glu Ser Gln Val Lys Ser
            260                 265                 270

Met Ser Thr Ser Leu Trp Lys Glu Asp Ser Thr Cys Phe Gln Trp Leu
```

```
                    275                 280                 285
His Lys Arg Glu Pro Asn Ser Val Val Tyr Val Asn Tyr Gly Ser Ile
            290                 295                 300
Thr Thr Met Thr Glu Asp Asn Phe Arg Glu Phe Ala Trp Gly Leu Ala
305                 310                 315                 320
Asn Ser Lys His Ser Phe Val Trp Ile Val Arg Pro Asp Val Ile Met
                325                 330                 335
Gly Ser Asn Ser Ala Thr Val Leu Pro Glu Glu Phe Phe Glu Glu Ile
            340                 345                 350
Lys Asp Arg Gly Leu Leu Ala Asn Trp Cys Gln Gln Lys Glu Val Leu
355                 360                 365
Glu His Ser Ser Val Gly Val Phe Leu Thr His Cys Gly Trp Asn Ser
    370                 375                 380
Thr Val Glu Thr Val Cys Ala Gly Val Pro Val Ile Cys Trp Pro Phe
385                 390                 395                 400
Phe Ala Asp Gln Gln Thr Asn Cys His Phe Ala Cys Lys Thr Leu Gly
                405                 410                 415
Ile Gly Val Glu Ile Ser Pro Asp Val Lys Arg Glu Val Thr Gly
            420                 425                 430
Leu Val Lys Glu Met Met Gly Glu Lys Gly Glu Lys Met Arg Glu
435                 440                 445
Lys Ala Ser Tyr Trp Lys Lys Lys Ala Ala Glu Thr Thr Asp Ile Gly
450                 455                 460
Gly Asp Ser Tyr His Asp Phe Asp Lys Leu Ile Lys Ser Leu Gly Phe
465                 470                 475                 480
Asp Gly Arg Asp

<210> SEQ ID NO 9
<211> LENGTH: 1470
<212> TYPE: DNA
<213> ORGANISM: Arabidopsis thaliana

<400> SEQUENCE: 9
atgggatctc agatcattca taactcacaa aaaccacatg tagtttgtgt tccatatccg      60
gctcaaggcc acatcaaccc tatgatgaga gtggctaaac tcctccacgc cagaggcttc     120
tacgtcacct tcgtcaacac cgtctacaac cacaatcgtt tccttcgttc tcgtgggtcc     180
aatgccctag atggacttcc ttcgttccga tttgagtcca ttgctgacgg tctaccagag     240
acagacatgg atgccacgca ggacatcaca gctctttgcg agtccaccat gaagaactgt     300
ctcgctccgt tcagagagct tctccagcgg atcaacgctg agataatgt tcctccggta      360 agctgtattg tatctgacgg ttgtatgagc tttactcttg atgttgcgga ggagcttgga     420
gtcccggagg ttcttttttg gacaaccagt ggctgtgcgt tcctggctta tctacacttt     480
tatctcttca tcgagaaggg cttatgtccg ctaaaagatg agagttactt gacgaaggag     540
tacttagaag acacggttat agattttata ccaaccatga agaatgtgaa actaaaggat     600
attcctagct tcatacgtac cactaatcct gatgatgtta tgattagttt cgccctccgc     660
gagaccgagc gagccaaacg tgcttctgct atcattctaa acacatttga tgaccttgag     720
catgatgttg ttcatgctat gcaatctatc ttacctccgg tttattcagt tggaccgctt     780
catctcttag caaaccggga gattgaagaa ggtagtgaga ttggaatgat gagttcgaat     840
ttatggaaag aggagatgga gtgtttggat tggcttgata ctaagactca aaatagtgtc     900
atttatatca actttgggag cataacggtt ttgagtgtga agcagcttgt ggagtttgct     960
```

```
tggggtttgg cgggaagtgg gaaagagttt ttatgggtga tccggccaga tttagtagcg   1020
ggagaggagg ctatggttcc gccggacttt ttaatgagac taaagaccg cagtatgcta   1080 gcgagttggt gtcctcaaga gaaagtactt tctcatcctg ctattggagg gtttttgacg   1140
cattgcgggt ggaactcgat attggaaagt ctttcgtgtg gagttccgat ggtgtgttgg   1200 ccatttttg ctgaccagca aatgaattgt aagttttgtt gtgacgagtg ggatgttggg   1260
attgagatag gtgagatgt gaagagagag aagttgagg cggtggttag agagctcatg   1320
gatggagaga agggaaagaa aatgagagaa aaggcggtag agtggcagcg cttagccgag   1380
aaagcgacgg aacataaact tggttcttcc gttatgaatt ttgagacggt tgttagcaag   1440
tttcttttgg gacaaaaatc acaggattaa                                    1470
```

```
<210> SEQ ID NO 10
<211> LENGTH: 1467
<212> TYPE: DNA
<213> ORGANISM: Arabidopsis thaliana

<400> SEQUENCE: 10
atgggatccc gttttgtttc taacgaacaa aaaccacacg tagtttgcgt gccttaccca     60
gctcaaggcc acattaaccc tatgatgaaa gtggctaaac tcctccacgt caaaggcttc    120
cacgtcacct tcgtcaacac cgtctacaac cacaaccgtc tactccgatc ccgtggggcc    180
aacgcactcg atggacttcc ttccttccag ttcgagtcaa tacctgacgg tcttccggag    240
actggcgtgg acgccacgca ggacatccct gccctttccg agtccacaac gaaaaactgt    300
ctcgttccgt tcaagaagct tctccagcgg attgtcacga gagaggatgt ccctccggtg    360
agctgtattg tatcagatgg ttcgatgagc tttactcttg acgtagcgga agagcttggt    420
gttccggaga ttcattttg gaccactagt gcttgtggct tcatggctta tctacacttt    480
tatctcttca tcgagaaggg tttatgtcca gtaaaagatg cgagttgctt gacgaaggaa    540
tacttggaca cagttataga ttggataccg tcaatgaaca atgtaaaact aaaagacatt    600
cctagtttta tacgtaccac taatcctaac gacataatgc tcaacttcgt tgtccgtgag    660
gcatgtcgaa ccaaacgtgc ctctgctatc attctgaaca cgtttgatga ccttgaacat    720
gacataatcc agtctatgca atccattta ccaccggttt atccaatcgg accgcttcat    780
ctcttagtaa acagggagat tgaagaagat agtgagattg aaggatggg atcaaatcta    840 tggaaagagg agactgagtg cttgggatgg cttaatacta agtctcgaaa tagcgttgtt    900
tatgttaact ttgggagcat aacaataatg accacggcac agcttttgga gtttgcttgg    960
ggtttggcgg caacgggaaa ggagtttcta tgggtgatgc ggccggattc agtagccgga   1020
gaggaggcag tgattccaaa agagttttta gcggagacag ctgatcgaag aatgctgaca   1080
agttggtgtc ctcaggagaa agttctttct catccggcgg tcggagggtt cttgacccat   1140
tgcgggtgga attcgacgtt agaaagtctt tcatgcggag ttccaatggt atgttggcca   1200
ttttttgctg agcaacaaac aaattgtaag ttttcttgtg atgaatggga ggttggtatt   1260
gagatcggtg gagatgtcaa gaggggagag gttgaggcgg tggttagaga gctcatggat   1320
ggagagaaag gaaagaaaat gagagagaag gctgtagagt ggcggcgctt ggccgagaaa   1380
gctacaaagc ttccgtgtgg ttcgtcggtg ataaattttg agacgattgt caacaaggtt   1440
ctcttgggaa agatccctaa cacgtaa                                       1467
```

```
<210> SEQ ID NO 11
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacccatatg ggatcccgtt ttgtttc                                          27

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcgagttac gtgttaggga tctttc                                           26

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacccatatg ggatctcaga tcattcataa c                                     31

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggatccttaa tcctgtgatt tttgtcccaa aag                                   33

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacccatatg accatggaaa ctaagcctca                                       30

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctcgagttat ggttttgatg atggcaccaa aac                                   33

<210> SEQ ID NO 17
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctcgagttat ggctttgatg atggcaccaa aac                                    33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggatccttag ggttttgaga gtggaaccaa tac                                    33

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cacccatatg ggttcaatca gcgaaatgat g                                      31

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggatccttag tccctaccat caaagc                                            26

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tttttttttt tttttttttt tttttttttt                                        30
```

MONOTERPENE GLYCOSYLTRANSFERASE ORIGINATING FROM HOP AND METHOD FOR USING SAME

SEQUENCE LISTING

The instant application contains a Sequence Listing which has been submitted electronically in ASCII format and is hereby incorporated by reference in its entirety. Said ASCII copy, created on Oct. 21, 2014, is named P46005_SL.txt and is 52,694 bytes in size.

TECHNICAL FIELD

The present invention relates to a protein having glycosylation activity on monoterpenes and a polynucleotide encoding this protein, a method for producing a monoterpene glycoside by means of this protein, a transformant that highly expresses monoterpene glycosyltransferase, as well as a monoterpene glycoside produced by the above method and use thereof. The present invention also relates to a plant modified to suppress the expression of a protein having glycosylation activity on a monoterpene compound and use thereof.

BACKGROUND ART

Terpenoids, particularly those with a relatively small molecular weight such as monoterpenes (C10) and sesquiterpenes (C15) serve as major aroma components in plants and are widely used not only as flavors for food products and/or alcoholic beverages, but also even in industrial products including cosmetics and perfumes. It is known that monoterpenes typified by linalool are synthesized within plant cells and are partially accumulated as glycosides. For example, in the case of *Arabidopsis thaliana* of the family Brassicaceae, a glycoside of hydroxylated linalool has been reported (Non-patent Document 1). Not only in model plants, but also in industrially important crops such as *Humulus lupulus* of the family Cannabaceae (Non-patent Document 2), *Camellia sinensis* of the family Theaceae (Non-patent Documents 3 to 6) and *Zingiber officinale* of the family Zingiberaceae (Non-patent Document 7), monoterpene glycosides are known to be accumulated. Further, because of being widely reported in the plant kingdom (Non-patent Document 8), glycosides would be a common form for precursors of aroma components. From the standpoint of industrial application, studies have also been conducted to artificially control the volatilization of aroma components from terpene glycosides serving as aroma precursors through enzymatic or non-enzymatic cleavage of their sugar moieties (Non-patent Document 9).

However, although β-primeverosidase, an enzyme cleaving the sugar moiety from a monoterpene glycoside, has been previously isolated from *Camellia sinensis* (Non-patent Document 10), molecular mechanisms for causing sugar addition (i.e., glycosylation) in monoterpenes have not yet been identified. Based on comprehensive activity screening of UDP-sugar dependent glycosyltransferases (UGTs) in *Arabidopsis thaliana*, some UGT enzymes have been reported to react with monoterpenes in test tubes, but there is no mention of their physiological roles and the significance of their activity (Non-patent Document 11). In *Citrus sinensis* of the family Rutaceae, monoterpene glycosides are also accumulated, and hence attempts have been made to screen UGTs acting on monoterpenes, but such attempts have not succeeded in identifying any active UGT enzyme gene (Non-patent Document 12).

*Humulus lupulus* of the family Cannabaceae is a major raw material for beer, and is produced mainly in Europe (e.g., Germany, Czech Republic) and North America (e.g., Canada, USA). Among aroma components responsible for the aroma of beer, those derived from *Humulus lupulus* include monoterpenes typified by linalool. On the cone surface of *Humulus lupulus*, there are trichomes called lupulin which are specifically differentiated to accumulate aroma components therein. Many aroma components are considered to be accumulated within lupulin. On the other hand, there are reports showing that glycosides of terpenes (e.g., glycosides of linalool and geraniol) are accumulated as precursors of aroma components in *Humulus lupulus* and beer, although enzymes for their production have not yet been identified (Non-patent Documents 2, 10 and 13).

Patent Document 1: WO97/11184
Non-patent Document 1: Aharoni et al (2003) Plant Cell 15, 2866-2884
Non-patent Document 2: Kollmannsberger et al (2006) Mschr. Brauwissenschaft 59, 83-89
Non-patent Document 3: Guo et al (1994) Biosci. Biotech. Biochem. 58, 1532-1534
Non-patent Document 4: Nishikitani et al (1996) Biosci. Biotech. Biochem. 60, 929-931
Non-patent Document 5: Moon et al (1996) Biosci. Biotech. Biochem. 60, 1815-1819
Non-patent Document 6: Ma et al (2001) Phytochemisty 56, 819-825
Non-patent Document 7: Sekiwa et al (1999) Biosci. Biotech. Biochem. 63, 384-389
Non-patent Document 8: Winterhalter and Skouroumounis (1997) Adv. Biochem. Eng. Biotechnol. 55, 73-105
Non-patent Document 9: Herrmann (2007) Angew. Chem. Int. Ed. 46, 5836-5863
Non-patent Document 10: Mizutani et al (2002) Plant Physiol. 130, 2164-2176
Non-patent Document 11: Caputi et al (2008) Chem. Eur. J. 14, 6656-6662
Non-patent Document 12: Fan et al (2010) Genome 53, 816-823
Non-patent Document 13: Nedjma, M., et al (2007) Congress Proceedings of European Brewery Convention 71, 1-13

DISCLOSURE OF THE INVENTION

As a result of extensive and intensive efforts, the inventors of the present invention have succeeded in identifying an enzyme catalyzing the glycosylation reaction of monoterpenes in *Humulus lupulus* and a gene sequence encoding this enzyme. The present invention is based on the above finding.

Namely, the present invention is as follows.
[1] A protein of any one selected from the group consisting of (a) to (c) shown below:
(a) a protein which consists of the amino acid sequence shown in SEQ ID NO: 2, 4 or 6;
(b) a protein which consists of an amino acid sequence with deletion, substitution, insertion and/or addition of 1 to 95 amino acids in the amino acid sequence shown in SEQ ID NO: 2, 4 or 6 and which has glycosylation activity on a monoterpene compound; and
(c) a protein which has an amino acid sequence sharing a sequence identity of 80% or more with the amino acid sequence shown in SEQ ID NO: 2, 4 or 6 and which has glycosylation activity on a monoterpene compound.

[2] The protein according to [1] above, wherein the monoterpene compound is geraniol or linalool.
[3] A polynucleotide of any one selected from the group consisting of (a) to (e) shown below:
(a) a polynucleotide containing the nucleotide sequence shown in SEQ ID NO: 1, 3 or 5;
(b) a polynucleotide encoding a protein which consists of the amino acid sequence shown in SEQ ID NO: 2, 4 or 6;
(c) a polynucleotide encoding a protein which consists of an amino acid sequence with deletion, substitution, insertion and/or addition of 1 to 95 amino acids in the amino acid sequence shown in SEQ ID NO: 2, 4 or 6 and which has glycosylation activity on a monoterpene compound;
(d) a polynucleotide encoding a protein which has an amino acid sequence sharing a sequence identity of 80% or more with the amino acid sequence shown in SEQ ID NO: 2, 4 or 6 and which has glycosylation activity on a monoterpene compound; and
(e) a polynucleotide which is hybridizable under high stringent conditions with a polynucleotide consisting of a nucleotide sequence complementary to the nucleotide sequence shown in SEQ ID NO: 1, 3 or 5 and which encodes a protein having glycosylation activity on a monoterpene compound.
[4] A non-human transformant transformed with the polynucleotide according to [3] above.
[5] The transformant according to [4] above, wherein the polynucleotide is inserted into an expression vector.
[6] The transformant according to [4] above, which is a whole plant.
[7] An extract of the transformant according to [4] above.
[8] A food, an aromatic, a pharmaceutical preparation or an industrial raw material, which comprises the extract according to [7] above.
[9] A method for producing a protein having glycosylation activity on a monoterpene compound, which comprises culturing the non-human transformant according to [4] above.
[10] A method for producing a monoterpene glycoside, which comprises the step of reacting the protein according to [1] above, a UDP-sugar and a monoterpene compound to cause glycosylation of the monoterpene compound.
[11] The method according to [10] above, wherein the UDP-sugar is UDP-glucose.
[12] The method according to [10] above, wherein the monoterpene compound is geraniol or linalool.

By using the protein of the present invention and a polynucleotide encoding this protein, glycosides of terpene compounds can be produced with high efficiency. Moreover, the transformants of the present invention are rich in glycosides of terpene compounds, and hence glycosides of terpene compounds can be efficiently extracted and purified from these transformants.

BEST MODES FOR CARRYING OUT THE INVENTION

Figure 1:
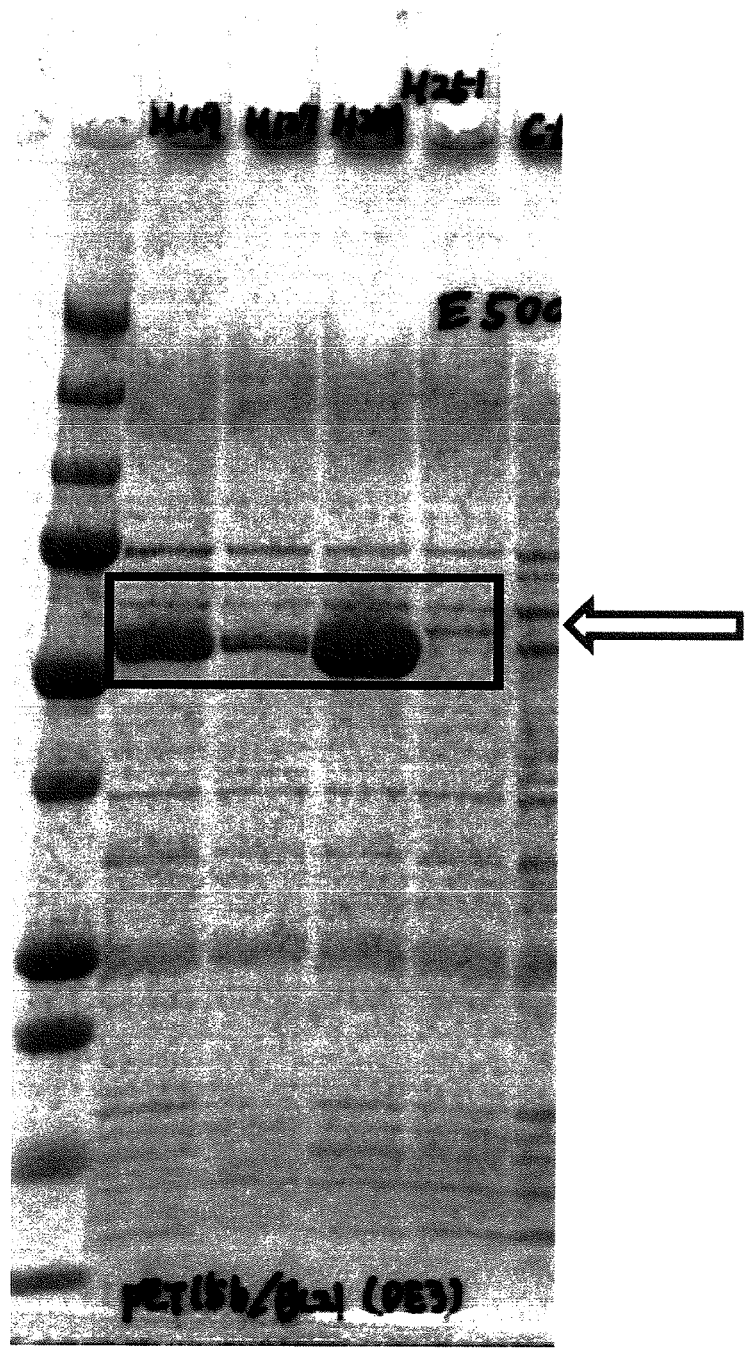
FIG. 1 shows the results (SDS-PAGE) analyzed for expression of *Humulus lupulus* HlUGT recombinant proteins.

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2012-022982 (filed on Feb. 6, 2012), based on which the present application claims priority.

The present invention will be described in more detail below. The following embodiments are illustrated to describe the present invention, and it is not intended to limit the present invention only to these embodiments. The present invention can be implemented in various modes, without departing from the spirit of the present invention.

The inventors of the present invention have elucidated, ahead of others, that enzyme proteins responsible for glycosylation reaction of monoterpene compounds in *Humulus lupulus* are HlUGT119, HlUGT127, HlUGT279 and HlUGT251.

The CDS sequence and deduced amino acid sequence of HlUGT119 are shown in SEQ ID NOs: 1 and 2, respectively. The CDS sequence and deduced amino acid sequence of HlUGT127 are shown in SEQ ID NOs: 3 and 4, respectively. Likewise, the CDS sequence and deduced amino acid sequence of HlUGT279 are shown in SEQ ID NOs: 5 and 6, respectively. Likewise, the CDS sequence and deduced amino acid sequence of HlUGT251 are shown in SEQ ID NOs: 7 and 8, respectively. These polynucleotides and enzymes can be obtained by procedures as described later in the Example section, known genetic engineering procedures, known synthesis procedures, etc.

1. *Humulus lupulus*-Derived Monoterpene Glycosyltransferase

The present invention provides a protein of any one selected from the group consisting of (a) to (c) shown below (hereinafter referred to as "the protein of the present invention"):
(a) a protein which consists of the amino acid sequence shown in SEQ ID NO: 2, 4, 6 or 8;
(b) a protein which consists of an amino acid sequence with deletion, substitution, insertion and/or addition of 1 to 95 amino acids in the amino acid sequence shown in SEQ ID NO: 2, 4, 6 or 8 and which has glycosylation activity on a monoterpene compound; and
(c) a protein which has an amino acid sequence sharing a sequence identity of 80% or more with the amino acid sequence shown in SEQ ID NO: 2, 4, 6 or 8 and which has glycosylation activity on a monoterpene compound.

In the above proteins (a) to (c), "the amino acid sequence shown in SEQ ID NO: 2, 4, 6 or 8" is intended in some embodiment to mean "the amino acid sequence shown in SEQ ID NO: 2, 4 or 6," "the amino acid sequence shown in SEQ ID NO: 2 or 4," "the amino acid sequence shown in SEQ ID NO: 2 or 6" or "the amino acid sequence shown in SEQ ID NO: 4 or 6."

In another embodiment, "the amino acid sequence shown in SEQ ID NO: 2, 4, 6 or 8" in the above proteins (a) to (c) is intended to mean "the amino acid sequence shown in SEQ ID NO: 8."

The above protein (b) or (c) is typically a mutant of the naturally occurring polypeptide shown in SEQ ID NO: 2, 4, 6 or 8, although other examples include those which may be artificially obtained by site-directed mutagenesis as described in "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

As used herein, the expression "protein which consists of an amino acid sequence with deletion, substitution, insertion and/or addition of 1 to 95 amino acids in the amino acid sequence shown in SEQ ID NO: 2, 4, 6 or 8 and which has glycosylation activity on a monoterpene compound" is intended to include proteins which consist of an amino acid sequence with deletion, substitution, insertion and/or addition of, e.g., 1 to 95 amino acid residues, 1 to 90 amino acid residues, 1 to 85 amino acid residues, 1 to 80 amino acid residues, 1 to 75 amino acid residues, 1 to 70 amino acid residues, 1 to 65 amino acid residues, 1 to 60 amino acid residues, 1 to 55 amino acid residues, 1 to 50 amino acid residues, 1 to 49 amino acid residues, 1 to 48 amino acid residues, 1 to 47 amino acid residues, 1 to 46 amino acid residues, 1 to 45 amino acid residues, 1 to 44 amino acid residues, 1 to 43 amino acid residues, 1 to 42 amino acid residues, 1 to 41 amino acid residues, 1 to 40 amino acid residues, 1 to 39 amino acid residues, 1 to 38 amino acid residues, 1 to 37 amino acid residues, 1 to 36 amino acid residues, 1 to 35 amino acid residues, 1 to 34 amino acid residues, 1 to 33 amino acid residues, 1 to 32 amino acid residues, 1 to 31 amino acid residues, 1 to 30 amino acid residues, 1 to 29 amino acid residues, 1 to 28 amino acid residues, 1 to 27 amino acid residues, 1 to 26 amino acid residues, 1 to 25 amino acid residues, 1 to 24 amino acid residues, 1 to 23 amino acid residues, 1 to 22 amino acid residues, 1 to 21 amino acid residues, 1 to 20 amino acid residues, 1 to 19 amino acid residues, 1 to 18 amino acid residues, 1 to 17 amino acid residues, 1 to 16 amino acid residues, 1 to 15 amino acid residues, 1 to 14 amino acid residues, 1 to 13 amino acid residues, 1 to 12 amino acid residues, 1 to 11 amino acid residues, 1 to 10 amino acid residues, 1 to 9 amino acid residues (one or several amino acid residues), 1 to 8 amino acid residues, 1 to 7 amino acid residues, 1 to 6 amino acid residues, 1 to 5 amino acid residues, 1 to 4 amino acid residues, 1 to 3 amino acid residues, 1 to 2 amino acid residues, or a single amino acid residue in the amino acid sequence shown in SEQ ID NO: 2, 4, 6 or 8 and which have glycosylation activity on a monoterpene compound. In general, a smaller number is more preferred for the above deletion, substitution, insertion and/or addition of amino acid residues.

Moreover, examples of such proteins include those which have an amino acid sequence sharing a sequence identity of 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence shown in SEQ ID NO: 2, 4, 6 or 8 and which have glycosylation activity on a monoterpene compound. In general, a larger value is more preferred for the above sequence identity.

In the context of the present invention, the phrase "glycosylation activity on a monoterpene compound" is intended to mean the ability to add a sugar included in a UDP-sugar to a hydroxy group in a monoterpene compound serving as an aglycon (i.e., glycosylation). There is no particular limitation on the position of the hydroxy group where sugar addition occurs.

Glycosylation activity on a monoterpene compound can be confirmed as follows: after incubation at a temperature of 20° C. to 40° C. in a neutral buffer of pH 6.0 to 8.0 (e.g., sodium phosphate buffer or potassium phosphate buffer) which contains the protein of the present invention in an amount of 1 to 500 ng (preferably 50 to 200 ng, most preferably 100 ng), a UDP-sugar (e.g., UDP-glucose) at 1 to 1000 µM (preferably 100 to 700 µM, most preferably 500 µM) and a monoterpene compound (e.g., linalool or geraniol) at 1 to 500 µM (preferably 100 to 500 µM, most preferably 250 µM), the above monoterpene is purified and analyzed by known procedures such as LC-MS analysis (liquid chromatography-mass spectrometry), etc.

Glycosylation reaction is normally completed within about 1 minute to about 12 hours.

Examples of interchangeable amino acid residues are shown below. Amino acid residues included in the same group are interchangeable with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine.

Although the protein of the present invention may be obtained by being expressed from a polynucleotide encoding it (see "the polynucleotide of the present invention" described later) in appropriate host cells, it may also be prepared by chemical synthesis methods such as Fmoc method (fluorenylmethyloxycarbonyl method) and tBoc method (t-butyloxycarbonyl method). Alternatively, the protein of the present invention may also be chemically synthesized with peptide synthesizers commercially available from Advanced Automation Peptide Protein Technologies, Perkin Elmer, Protein Technologies, PerSeptive, Applied Biosystems, SHIMADZU, etc.

In the context of the present invention, the term "monoterpene compound" refers to a hydrocarbon containing isoprene

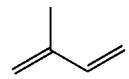

as a constituent unit and encompasses not only biosubstances produced, e.g., by plants, insects and fungi, but also chemically synthesized compounds.

In the present invention, any monoterpene compound can be used as long as it has a hydroxy group (e.g., linalool or geraniol).

Examples of such a monoterpene include, but are not limited to, nerol, geraniol and linalool. Preferred is geraniol or linalool.

For example, *Humulus lupulus*-derived geraniol has an —OH group at the 1-position, while *Humulus lupulus*-derived linalool has an —OH group at the 3-position. Thus, when the protein of the present invention is used for glycosylation of geraniol contained in *Humulus lupulus* cells, sugar addition will occur in the —OH group at the 1-position. Likewise, when the protein of the present invention is used for glycosylation of linalool contained in *Humulus lupulus* cells, sugar addition will occur in the —OH group at the 3-position.

TABLE 1

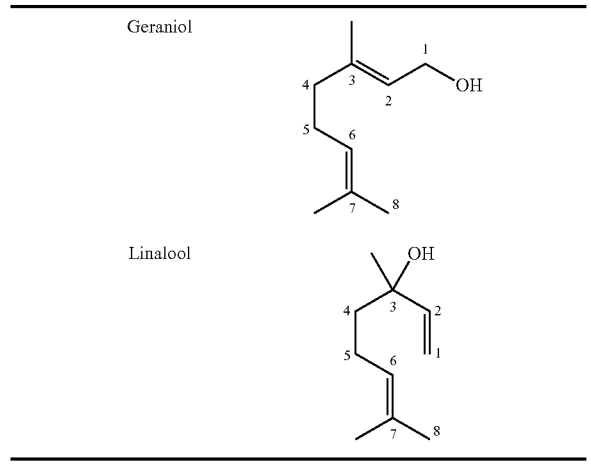

In the context of the present invention, the term "UDP-sugar" refers to a uridine diphosphate (UDP)-conjugated sugar, and examples include, but are not limited to, UDP-glucuronic acid and UDP-glucose. A preferred UDP-sugar is UDP-glucose.

2. Method for Producing a Monoterpene Glycoside

The present invention allows easy and large-scale production of monoterpene glycosides by means of the protein's glycosylation activity on monoterpene compounds.

In another embodiment, the present invention therefore provides a method for producing a glycoside of a monoterpene compound, which comprises the step of reacting the protein of the present invention, a UDP-sugar and a monoterpene compound to cause glycosylation of the monoterpene compound.

In the method of the present invention for producing a monoterpene glycoside, the UDP-sugar is preferably exemplified by UDP-glucose, while the monoterpene compound is preferably geraniol or linalool.

The method of the present invention for producing a monoterpene glycoside comprises the step of reacting the protein of the present invention, a UDP-sugar and a monoterpene compound to cause glycosylation of the monoterpene compound. The method of the present invention may further comprise the step of purifying the glycoside of the monoterpene compound generated in the above step.

The glycoside of the monoterpene compound can be purified by known techniques such as extraction with an appropriate solvent (an aqueous solvent such as water or an organic solvent such as alcohol, ether or acetone), a gradient between an organic solvent (e.g., ethyl acetate) and water, high performance liquid chromatography (HPLC), gas chromatography, time-of-flight mass spectrometry (TOF-MS), ultra (high) performance liquid chromatography (UPLC), etc.

3. Non-Human Transformant Rich in Monoterpene Glycosides

Monoterpene glycosides may also be produced using the protein of the present invention within cells such as those of bacteria (e.g., *E. coli* or yeast), plants, insects, non-human mammals, etc. This is because the protein of the present invention is an enzyme derived from *Humulus lupulus* or a mutant thereof and is therefore expected to have high activity even in the intracellular environment. In this case, a polynucleotide encoding the protein of the present invention (see "the polynucleotide of the present invention" described later) may be introduced into host cells derived from bacteria, plants, insects, non-human mammals or the like to cause expression of the protein of the present invention, followed by reacting the protein of the present invention with UDP-sugars and monoterpene compounds present within the above cells to produce monoterpene glycosides.

The present invention therefore provides a non-human transformant transformed with a polynucleotide of any one selected from the group consisting of (a) to (e) shown below (hereinafter referred to as "the polynucleotide of the present invention") (such a transformant is hereinafter referred to as "the transformant of the present invention"):

(a) a polynucleotide containing the nucleotide sequence shown in SEQ ID NO: 1, 3, 5 or 7;

(b) a polynucleotide encoding a protein which consists of the amino acid sequence shown in SEQ ID NO: 2, 4, 6 or 8;

(c) a polynucleotide encoding a protein which consists of an amino acid sequence with deletion, substitution, insertion and/or addition of 1 to 95 amino acids in the amino acid sequence shown in SEQ ID NO: 2, 4, 6 or 8 and which has glycosylation activity on a monoterpene compound;

(d) a polynucleotide encoding a protein which has an amino acid sequence sharing a sequence identity of 80% or more with the amino acid sequence shown in SEQ ID NO: 2, 4, 6 or 8 and which has glycosylation activity on a monoterpene compound; and (e) a polynucleotide which is hybridizable under high stringent conditions with a polynucleotide consisting of a nucleotide sequence complementary to the nucleotide sequence shown in SEQ ID NO: 1, 3, 5 or 7 and which encodes a protein having glycosylation activity on a monoterpene compound.

In the above polynucleotides (b) to (d), "the amino acid sequence shown in SEQ ID NO: 2, 4, 6 or 8" is intended in some embodiment to mean "the amino acid sequence shown in SEQ ID NO: 2, 4 or 6," "the amino acid sequence shown in SEQ ID NO: 2 or 4," "the amino acid sequence shown in SEQ ID NO: 2 or 6" or "the amino acid sequence shown in SEQ ID NO: 4 or 6."

In another embodiment, "the amino acid sequence shown in SEQ ID NO: 2, 4, 6 or 8" in the above polynucleotides (b) to (d) is intended to mean "the amino acid sequence shown in SEQ ID NO: 8."

In the above polynucleotides (a) and (e), "the nucleotide sequence shown in SEQ ID NO: 1, 3, 5 or 7" is intended in some embodiment to mean "the nucleotide sequence shown in SEQ ID NO: 1, 3 or 5," "the nucleotide sequence shown in SEQ ID NO: 1 or 3," "the nucleotide sequence shown in SEQ ID NO: 1 or 5" or "the nucleotide sequence shown in SEQ ID NO: 3 or 5."

In another embodiment, "the nucleotide sequence shown in SEQ ID NO: 1, 3, 5 or 7" in the above polynucleotides (a) and (e) is intended to mean "the nucleotide sequence shown in SEQ ID NO: 7."

As used herein, the term "polynucleotide" is intended to mean DNA or RNA.

As used herein, the expression "polynucleotide which is hybridizable under high stringent conditions" is intended to mean, for example, a polynucleotide that can be obtained by means of colony hybridization, plaque hybridization, Southern hybridization or other hybridization techniques using, as a probe, the whole or a part of a polynucleotide consisting of a nucleotide sequence complementary to the nucleotide sequence shown in SEQ ID NO: 1, 3, 5 or 7 or of a polynucleotide consisting of a nucleotide sequence encoding the amino acid sequence shown in SEQ ID NO: 2, 4, 6 or 8. For hybridization, it is possible to use techniques as described in, e.g., "Sambrook & Russell, Molecular Cloning: A Laboratory Manual Vol. 3, Cold Spring Harbor, Laboratory Press 2001" and "Ausubel, Current Protocols in Molecular Biology, John Wiley & Sons 1987-1997."

As used herein, the term "high stringent conditions" refers to, for example, but is not limited to, conditions of 5×SSC, 5×Denhardt's solution, 0.5% SDS, 50% formamide, 50° C. or 0.2×SSC, 0.1% SDS, 60° C., 0.2×SSC, 0.1% SDS, 62° C., 0.2×SSC, 0.1% SDS, 65° C. Under these conditions, it can be expected that DNA having a higher sequence identity is efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that if a commercially available kit is used for hybridization, an Alkphos Direct Labelling and Detection System (GE Healthcare) may be used for this purpose, by way of example. In this case, hybridization may be accomplished in accordance with the protocol attached to the kit, i.e., a membrane may be incubated overnight with a labeled probe and then washed with a primary washing buffer containing 0.1% (w/v) SDS under conditions of 55° C. to 60° C. to detect the hybridized DNA. Alternatively, if a commercially available reagent (e.g., PCR labeling mix (Roche Diagnostics)) is used for digoxigenin (DIG) labeling of a probe during probe preparation based on the whole or a part of a nucleotide sequence complementary to the nucleotide sequence shown in SEQ ID NO: 1, 3, 5 or 7, or of a nucleotide sequence encoding the amino acid sequence shown in SEQ ID NO: 2, 4, 6 or 8, a DIG nucleic acid detection kit (Roche Diagnostics) may be used for detection of hybridization.

In addition to those listed above, other hybridizable polynucleotides include DNAs sharing a sequence identity of 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with DNA shown in SEQ ID NO: 1, 3, 5 or 7 or with DNA encoding the amino acid sequence shown in SEQ ID NO: 2, 4, 6 or 8, as calculated by homology search software such as FASTA or BLAST using default parameters.

It should be noted that the sequence identity of amino acid sequences or nucleotide sequences can be determined by using FASTA (Science 227 (4693): 1435-1441, (1985)) or the algorithm of Karlin and Altschul, BLAST (Basic Local Alignment Search Tool) (Proc. Natl. Acad. Sci. USA 872264-2268, 1990; Proc Natl Acad Sci USA 90: 5873, 1993). Based on the algorithm of BLAST, programs called blastn, blastx, blastp, tblastn and tblastx have been developed (Altschul S F, et al: J Mol Biol 215: 403, 1990). If blastn is used for nucleotide sequence analysis, parameters may be set to, for example, score=100 and wordlength=12.

Likewise, if blastp is used for amino acid sequence analysis, parameters may be set to, for example, score=50 and wordlength=3. If BLAST and Gapped BLAST programs are used, default parameters in each program may be used.

The above polynucleotides according to the present invention can be obtained by known genetic engineering procedures or known synthesis procedures.

The polynucleotide of the present invention is preferably introduced into a host in a state of being inserted into an appropriate expression vector.

An appropriate expression vector is generally configured to comprise:
(i) a promoter transcribable in host cells;
(ii) the polynucleotide of the present invention ligated to the promoter; and
(iii) an expression cassette comprising, as constituent elements, signals that function in the host cells for transcription termination and polyadenylation of an RNA molecule.

Such an expression vector may be prepared in any manner, for example, by techniques using plasmids, phages or cosmids, etc.

The actual type of vector is not limited in any way, and any vector expressible in host cells may be selected as appropriate. Namely, a promoter sequence may be selected as appropriate for the type of host cells in order to ensure expression of the polynucleotide of the present invention, and this promoter and the polynucleotide of the present invention may then be integrated into various plasmids or the like for use as expression vectors.

The expression vector of the present invention contains an expression control region(s) (e.g., a promoter, a terminator and/or a replication origin), depending on the type of host into which the expression vector is to be introduced. Promoters for use in bacterial expression vectors may be commonly used promoters (e.g., trc promoter, tac promoter, lac promoter). Likewise, promoters for use in yeast include, for example, glyceraldehyde triphosphate dehydrogenase promoter, PH05 promoter and so on, while promoters for use in filamentous fungi include, for example, amylase, trpC and so on. In addition, examples of promoters used to express a desired gene in plant cells include cauliflower mosaic virus 35S RNA promoter, rd29A gene promoter, rbcS promoter, and mac-1 promoter that is configured to have the enhancer sequence of the above cauliflower mosaic virus 35S RNA promoter at the 5'-side of *Agrobacterium*-derived mannopine synthase promoter sequence. Examples of promoters for use in animal cell hosts include viral promoters (e.g., SV40 early promoter, SV40 late promoter) and so on.

The expression vector preferably comprises at least one selection marker. For this purpose, auxotrophic markers (ura5, niaD), drug resistance markers (hygromycine, zeocin), geneticin resistance gene (G418r), copper resistance gene (CUP 1) (Marin et al., Proc. Natl. Acad. Sci. USA, vol. 81, p. 337, 1984), cerulenin resistance genes (fas2m, PDR4) (Junji Inokoshi et al., Biochemistry, vol. 64, p. 660, 1992; Hussain et al., Gene, vol. 101, p. 149, 1991) and so on are available for use.

Although the transformant of the present invention may be prepared (produced) in any manner, an expression vector comprising the polynucleotide of the present invention may be introduced into a host to transform the host, by way of example. Host cells used for this purpose may be of any type, and conventionally known various types of cells can be used preferably. Specific examples include bacteria such as *E. coli*, yeast (budding yeast *Saccharomyces cerevisiae*, fission yeast *Schizosaccharomyces pombe*), plant cells, non-human animal cells and so on.

Culture media and conditions appropriate for the above host cells are well known in the art. Moreover, the organism to be transformed may be of any type, and examples include various types of microorganisms or plants or non-human animals as listed above for host cells.

For transformation of host cells, commonly used known techniques can be used. For example, transformation may be accomplished by, but is not limited to, electroporation (Mackenxie, D. A. et al., Appl. Environ. Microbiol., vol. 66, p. 4655-4661, 2000), particle delivery method (described in JP 2005-287403 A entitled "Breeding Method of Lipid Producing Fungi"), spheroplast method (Proc. Natl. Acad. Sci. USA, vol. 75, p. 1929, 1978), lithium acetate method (J. Bacteriology, vol. 153, p. 163, 1983), and other methods as described in Methods in yeast genetics, 2000 Edition: A Cold Spring Harbor Laboratory Course Manual.

In addition, as for standard molecular biological procedures, reference may be made to "Sambrook & Russell, Molecular Cloning: A Laboratory Manual Vol. 3, Cold Spring Harbor Laboratory Press 2001," "Methods in Yeast Genetics, A laboratory manual (Cold Spring Harbor Laboratory Press, Cold Spring Harbor, N.Y.)," etc.

In one embodiment of the present invention, the transformant may be a plant transformant. The plant transformant according to this embodiment may be obtained by introducing a recombinant vector comprising the polynucleotide of the present invention into a plant such that a polypeptide encoded by this polynucleotide can be expressed.

In cases where a recombinant expression vector is used, any recombinant expression vector may be used for transformation of a whole plant as long as it is a vector allowing the polynucleotide of the present invention to be expressed within the plant. Examples of such a vector include those having a promoter which drives constitutive expression of a desired polynucleotide within plant cells or those having a promoter whose activation is induced by external stimulation.

Examples of a promoter which drives constitutive expression of a desired polynucleotide within plant cells include cauliflower mosaic virus 35S RNA promoter, rd29A gene promoter, rbcS promoter, mac-1 promoter, etc.

Examples of a promoter whose activation is induced by external stimulation include mouse mammary tumor virus (MMTV) promoter, tetracycline-responsive promoter, metallothionein promoter and heat shock protein promoter, etc.

The plant to be transformed in the present invention is intended to mean any of a whole plant, a plant organ (e.g., leaf, petal, stem, root, seed), a plant tissue (e.g., epidermis, phloem, parenchyma, xylem, vascular bundle, palisade tissue, spongy parenchyma) or a plant cultured cell, or alternatively, various forms of plant cells (e.g., suspension cultured cells), a protoplast, a leaf section, a callus and so on. The plant used for transformation may be of any type, belonging to either monocotyledons or dicotyledons.

For gene transfer into plants, transformation techniques known to those skilled in the art may be used (e.g., *Agrobacterium*-mediated method, gene gun method, PEG-mediated method, electroporation). For example, *Agrobacterium*-mediated method and direct gene transfer into plant cells are well known. In the case of using the *Agrobacterium*-mediated method, the constructed plant expression vector may be introduced into an appropriate *Agrobacterium* strain (e.g., *Agrobacterium tumefaciens*) and this strain may then be infected into a leaf section cultured under sterile conditions, e.g., in accordance with the leaf disk method (Hirofumi Miyauchi, Manuals for Plant Genetic Engineering (1990) pages 27-31, Kodansha Scientific Ltd., Tokyo) to thereby obtain a transgenic plant. Alternatively, it is possible to use the method of Nagel et al. (Micribiol. Lett., 67: 325 (1990)). In this method, for example, an expression vector is first introduced into *Agrobacterium*, and the transformed *Agrobacterium* is then introduced into plant cells or plant tissues as described in Plant Molecular Biology Manual (Gelvin, S. B. et al., Academic Press Publishers). As used herein, the term "plant tissue" also includes a callus obtainable by culturing plant cells. In cases where the *Agrobacterium*-mediated method is used for transformation, a binary vector (e.g., pBI121 or pPZP202) may be used.

Likewise, techniques known for direct gene transfer into plant cells or plant tissues are electroporation and particle gun method. In the case of using a particle gun, a whole plant, a plant organ or a plant tissue may be used directly, or sections may be prepared therefrom before use, or protoplasts may be prepared and used. The thus prepared samples may be treated using a gene transfer device (e.g., PDS-1000 (BIO-RAD)). Although treatment conditions will vary depending on the type of plant or sample, the treatment is generally conducted at a pressure of about 450 to 2000 psi and at a distance of about 4 to 12 cm.

The transformed cells or plant tissues are first selected by drug resistance such as hygromycin resistance, and then regenerated into whole plants in a standard manner. Regeneration from transformed cells into whole plants may be accomplished by techniques known to those skilled in the art as appropriate for the type of plant cells.

In cases where cultured plant cells are used as a host, transformation may be accomplished by introducing a recombinant vector into the cultured cells with a gene gun or by electroporation, etc. Calli, shoots, hairy roots and the like obtained as a result of transformation may be used directly for cell culture, tissue culture or organ culture, and may also be regenerated into whole plants using conventionally known procedures for plant tissue culture, e.g., by being administered with an appropriate concentration of a plant hormone (e.g., auxin, cytokinin, gibberellin, abscisic acid, ethylene, brassinolide).

Confirmation of whether or not the polynucleotide of the present invention has been introduced into a plant may be accomplished by PCR, Southern hybridization, Northern hybridization, etc. For example, DNA is prepared from a transgenic plant and DNA specific primers are designed for PCR. PCR may be performed under the same conditions as used for preparation of the above plasmid. Then, amplification products may be subjected to, e.g., agarose gel electrophoresis, polyacrylamide gel electrophoresis or capillary electrophoresis, followed by staining with ethidium bromide, SYBR Green solution, etc. If the amplification products are detected as a single band, it can be confirmed that the plant has been transformed. Alternatively, primers which have been labeled with a fluorescent dye or the like may be used in PCR to thereby detect amplification products. Further, it is also possible to use techniques in which amplification products are bound onto a solid phase (e.g., a microplate) and confirmed by fluorescence or enzymatic reaction, etc.

Once a transgenic whole plant whose genome carries the polynucleotide of the present invention has been obtained, progeny plants may be obtained by sexual or asexual reproduction of the whole plant. Moreover, from such a whole plant or progeny plants thereof or clones thereof, for example, seeds, fruits, cuttings, tubers, root tubers, rootstocks, calli, protoplasts or the like may be obtained and used to achieve mass production of the whole plant. Thus, the present invention also encompasses a whole plant into which the polynucleotide of the present invention has been introduced in an expressible form, or progeny plants of the whole plant which have the same properties as the whole plant, or tissues derived from the whole plant and progeny plants thereof.

In addition, transformation techniques for various plants have already been reported. Transgenic plants according to the present invention include plants of the family Solanaceae (e.g., eggplant, tomato, hot pepper, potato, tobacco, stramonium, Chinese lantern plant, petunia, calibrachoa, nierembergia), plants of the family Leguminosae (e.g., soybean, adzuki bean, peanut, kidney bean, broad bean, Bird's foot trefoil), plants of the family Rosaceae (e.g., strawberry, Japanese apricot, cherry tree, rose, blueberry, blackberry, bilberry, cassis, raspberry), plants of the family Caryophyllaceae (e.g., carnation, gypsophila), plants of the family Asteraceae (e.g., chrysanthemum, gerbera, sunflower, daisy), plants of the family Orchidaceae (e.g., orchid), plants of the family Primulaceae (e.g., cyclamen), plants of the family Gentianaceae (e.g., showy prairie gentian, gentian), plants of the family Iridaceae (e.g., freesia, iris, gladiolus), plants of the family Scrophulariaceae (e.g., snapdragon, torenia), stone crop (kalanchoe), plants of the family Liliaceae (e.g., lily, tulip), plants of the family Convolvulaceae (e.g., morning glory, ivy-leaved morning glory, moonflower, sweet potato, cypress vine, evolvulus), plants of the family Hydrangeaceae (e.g., hydrangea, deutzia), plants of the family Cucurbitaceae (e.g., bottle gourd), plants of the family Geraniaceae (e.g., pelargonium, geranium), plants of the family Oleaceae (e.g., weeping forsythia), plants of the family Vitaceae (e.g., grape), plants of the family Theaceae (e.g., *camellia*, tea plant), plants of the family Gramineae (e.g., rice, barley, wheat, oat, rye, maize, foxtail millet, Japanese barnyard millet, kaoliang, sugar cane, bamboo, wild oat, finger millet, sorghum, Manchurian wild rice, job's tears, pasture grass), plants of the family Moraceae (e.g., mulberry, hop, paper mulberry, rubber tree, cannabis), plants of the family Rubiaceae (e.g., coffee tree, gardenia), plants of the family Fagaceae (e.g., oak, beech, Japanese emperor oak), plants of the family Pedaliaceae (e.g., sesame), plants of the family Rutaceae (e.g., bitter orange, *Citrus junos*, satsuma mandarin, Japanese pepper tree), plants of the family Brassicaceae (e.g., red cabbage, flowering cabbage, Japanese radish, white shepherd's purse, Chinese colza, cabbage, broccoli, cauliflower), and plants of the family Lamiacea (e.g., salvia, perilla, lavender, skullcap). Examples of preferred plants include aromatic plants (e.g., perilla and lavender), as well as garden plants (e.g., carnation) which are inherently less aromatic but are of high commercial value.

The whole plant transformed with the polynucleotide of the present invention (hereinafter referred to as "the plant of the present invention" or "the whole plant of the present invention") is rich in glycosides of monoterpene compounds when compared to the wild-type counterpart.

The plant of the present invention can be easily obtained as a perfect whole plant by being grown from a seed, a cuttage, a bulb or the like of the plant of the present invention.

Thus, the plant of the present invention encompasses a whole plant, a plant organ (e.g., leaf, petal, stem, root, seed, bulb), a plant tissue (e.g., epidermis, phloem, parenchyma, xylem, vascular bundle, palisade tissue, spongy parenchyma) or a cultured plant cell, or alternatively, various forms of plant cells (e.g., suspension cultured cells), a protoplast, a leaf section, a callus and so on.

4. Extract of Transformant and Use Thereof

In another embodiment, the present invention also provides an extract of the above transformant. Since the transformant of the present invention is rich in monoterpene glycosides when compared to the wild-type counterpart, an extract of the transformant is considered to contain monoterpene glycosides at high concentrations.

Such an extract of the transformant of the present invention can be obtained as follows: the transformant is homogenized with, e.g., glass beads, a homogenizer or a sonicator and the resulting homogenate is centrifuged to collect the supernatant. In addition, a further extraction step may also be provided in accordance with extraction procedures for monoterpene glycosides as mentioned above.

The extract of the transformant of the present invention can be provided for use in, e.g., production of foods, aromatics, pharmaceutical preparations and/or industrial raw materials (e.g., raw materials for cosmetics, soaps, etc.) according to standard practice.

In another embodiment, the present invention also provides a food, an aromatic, a pharmaceutical preparation and/or an industrial raw material (e.g., raw materials for cosmetics, soaps, etc.), each containing the extract of the transformant of the present invention. Such a food, an aromatic, a pharmaceutical preparation and/or an industrial raw material, each containing the extract of the transformant of the present invention, may be prepared in a routine manner. In this way, such a food, an aromatic, a pharmaceutical preparation and/or an industrial raw material, each containing the extract of the transformant of the present invention, contains monoterpene glycosides generated by using the transformant of the present invention.

The aromatic (composition) or pharmaceutical preparation (composition) of the present invention may be in any dosage form, such as solution, paste, gel, solid, powder and other dosage forms. Moreover, the aromatic composition or pharmaceutical composition of the present invention may be used in cosmetics or external preparations for skin (e.g., oil, lotion, cream, emulsion, gel, shampoo, hair conditioner, nail enamel, foundation, lipstick, face powder, facial pack, ointment, perfume, powder, eau de cologne, dentifrice, soap, aerosol, cleansing foam), as well as bath preparations, hair growth promoters, skin essences, sunscreening agents and so on.

When required, the cosmetic composition of the present invention may further be blended as appropriate with additional ingredients such as fats or oils, and/or dyes, aromatics, antiseptics, surfactants, pigments, antioxidants, etc. The blending ratio of these ingredients may be determined by those skilled in the art as appropriate for the intended purpose (e.g., fats or oils may be contained in the composition at a ratio of 1% to 99.99% by weight, preferably 5% to 99.99% by weight, more preferably 10% to 99.95% by weight). Likewise, the pharmaceutical composition of the present invention may further comprise additional pharmaceutically active ingredients (e.g., anti-inflammatory ingredient) or auxiliary ingredients (e.g., lubricating ingredient, carrier ingredient), when required.

Examples of the food of the present invention include nutritional supplementary foods, health foods, functional foods, children's foods, geriatric foods and so on. The term "food" or "food product" is used herein as a generic name for edible materials in the form of solids, fluids, liquids or mixtures thereof.

The term "nutritional supplementary foods" refers to food products enriched with specific nutritional ingredients. The term "health foods" refers to food products that are healthful or good for health, and encompasses nutritional supplementary foods, natural foods and diet foods. The term "functional foods" refers to food products for replenishing nutritional ingredients which assist body control functions. Functional foods are synonymous with foods for specified health use. The term "children's foods" refers to food products given to children up to about 6 years old. The term "geriatric foods" refers to food products treated to facilitate digestion and absorption when compared to untreated foods.

These foods and food products may be in the form of agricultural foods including bakery products, noodles, cooked rice, sweets (e.g., candies, chewing gums, gummies, tablets, Japanese sweets), bean curd and processed products thereof; fermented foods including Japanese rice wine (sake), medicinal liquor, sweet cooking sherry (mirin), vinegar, soy sauce and miso (bean paste); livestock food products including yogurt, ham, bacon and sausage; seafood products including fish cake (kamaboko), deep-fried fish cake (ageten) and puffy fish cake (hanpen); as well as fruit drinks, soft drinks, sports drinks, alcoholic beverages, tea or flavor enhancers.

5. Plant Modified to Suppress the Expression of Monoterpene Glycosyltransferase

When suppressing the expression of a protein endogenously occurring in plants and having glycosylation activity on monoterpene compounds, monoterpenes are inhibited from being glycosylated. As a result, such a plant will contain more monoterpenes in the form of aglycon and can be expected to release a stronger aroma.

The present invention therefore provides a plant modified to suppress the expression of a protein having glycosylation activity on monoterpene compounds.

More specifically, such a protein having glycosylation activity on monoterpene compounds (hereinafter referred to as "monoterpene glycosyltransferase") is encoded by a polynucleotide of any one selected from the group consisting of (a) to (e) shown below:
(a) a polynucleotide containing the nucleotide sequence shown in SEQ ID NO: 1, 3, 5 or 7;
(b) a polynucleotide encoding a protein which consists of the amino acid sequence shown in SEQ ID NO: 2, 4, 6 or 8;
(c) a polynucleotide encoding a protein which consists of an amino acid sequence with deletion, substitution, insertion and/or addition of 1 to 95 amino acids in the amino acid sequence shown in SEQ ID NO: 2, 4, 6 or 8 and which has glycosylation activity on a monoterpene compound;
(d) a polynucleotide encoding a protein which has an amino acid sequence sharing a sequence identity of 80% or more with the amino acid sequence shown in SEQ ID NO: 2, 4, 6 or 8 and which has glycosylation activity on a monoterpene compound; and
(e) a polynucleotide which is hybridizable under high stringent conditions with a polynucleotide consisting of a nucleotide sequence complementary to the nucleotide sequence shown in SEQ ID NO: 1, 3, 5 or 7 and which encodes a protein having glycosylation activity on a monoterpene compound.

In the above polynucleotides (b) to (d), "the amino acid sequence shown in SEQ ID NO: 2, 4, 6 or 8" is intended in some embodiment to mean "the amino acid sequence shown in SEQ ID NO: 2, 4 or 6," "the amino acid sequence shown in SEQ ID NO: 2 or 4," "the amino acid sequence shown in SEQ ID NO: 2 or 6" or "the amino acid sequence shown in SEQ ID NO: 4 or 6."

In another embodiment, "the amino acid sequence shown in SEQ ID NO: 2, 4, 6 or 8" in the above polynucleotides (b) to (d) is intended to mean "the amino acid sequence shown in SEQ ID NO: 8."

In the above polynucleotides (a) and (e), "the nucleotide sequence shown in SEQ ID NO: 1, 3, 5 or 7" is intended in some embodiment to mean "the nucleotide sequence shown in SEQ ID NO: 1, 3 or 5," "the nucleotide sequence shown in SEQ ID NO: 1 or 3," "the nucleotide sequence shown in SEQ ID NO: 1 or 5" or "the nucleotide sequence shown in SEQ ID NO: 3 or 5."

In another embodiment, "the nucleotide sequence shown in SEQ ID NO: 1, 3, 5 or 7" in the above polynucleotides (a) and (e) is intended to mean "the nucleotide sequence shown in SEQ ID NO: 7."

The polynucleotides (a) to (e) are as defined above in "3. Non-human transformant rich in monoterpene glycosides."

Specific examples of means to suppress the expression of monoterpene glycosyltransferase include substances capable of reducing the expression level of messenger RNA (mRNA) for this enzyme, as exemplified by low molecular compounds, hormones, proteins and nucleic acids. In one embodiment, such a substance may be a nucleic acid capable of suppressing the functions or expression of a gene encoding the above enzyme. Examples of such a nucleic acid include hairpin-shaped shRNAs (short hairpin RNAs) or double-stranded RNAs (dsRNAs) which produce siRNAs (small interfering RNAs) for RNA interference (RNAi), as well as antisense nucleic acids, decoy nucleic acids, or aptamers, etc. These inhibitory nucleic acids are able to suppress the expression of the above gene. The target gene to be inhibited which encodes monoterpene glycosyltransferase consists of any one of the above polynucleotides (a) to (e), and sequence information can be obtained for each polynucleotide. In the present invention, it is possible to use, as a target region to be inhibited, not only a coding region, but also a non-coding region of the gene encoding monoterpene glycosyltransferase.

RNA interference (RNAi) is a multi-step process proceeding through a number of stages. First of all, dsRNA or shRNA expressed from an RNAi expression vector is recognized by Dicer and cleaved into siRNAs of 21 to 23 nucleotides. These siRNAs are then integrated into an RNAi targeting complex, which is called the RNA-induced silencing complex (RISC), and the complexes between RISC and siRNAs bind to target mRNA containing sequences complementary to the siRNA sequences and thereby cleave the mRNA. The target mRNA is cleaved in the center of its region complementary to the siRNA, finally leading to rapid degradation of the target mRNA and reduced protein expression levels. The most potent siRNA duplexes are known to be sequences of 21 nucleotides in length, each comprising a 19 bp duplex with an overhang of two uridine residues at the 3'-terminal end (Elbashir S. M. et al., Genes and Dev, 15, 188-200 (2001)).

In general, a target sequence on mRNA may be selected from the cDNA sequence corresponding to the mRNA. However, the present invention is not limited to this region.

siRNA molecules may be designed on the basis of the criteria well known in the art. For example, as a target segment in target mRNA, it is possible to select a segment covering 15 to 30 contiguous bases, preferably 19 to 25 contiguous bases, preferably starting with AA, TA, GA or CA. siRNA molecules have a GC ratio of 30% to 70%, preferably 35% to 55%. Alternatively, a target sequence for RNAi may be selected as appropriate as described in Ui-Tei K. et al. ((2004) Nucleic Acids Res. 32, 936-948).

For introduction of siRNA into cells, it is possible to use, e.g., procedures in which synthesized siRNA is ligated to plasmid DNA and then introduced into cells, or procedures in which double-stranded RNA is annealed.

In the present invention, shRNA may also be used for providing RNAi effect. shRNA is an RNA molecule called short hairpin RNA, which has a stem-loop structure because some single-stranded regions form complementary strands with other regions.

shRNA may be designed to form a stem-loop structure as a part thereof. For example, assuming that a sequence covering a certain region is designated as sequence A, and a strand complementary to the sequence A is designated as sequence B, shRNA is designed to comprise the sequence A, a spacer and the sequence B linked in this order on a single RNA strand and to have an overall length of 45 to 60 bases. The spacer may also have any length.

Although the sequence A is a sequence covering a partial region of the target gene encoding monoterpene glycosyltransferase, there is no particular limitation on the target region and any region may be selected as a candidate for the target region. In addition, the sequence A has a length of 19 to 25 bases, preferably 19 to 21 bases.

Further, in the present invention, microRNA may be used to inhibit the expression of monoterpene glycosyltransferase. microRNA (miRNA) is an intracellular single-stranded RNA molecule having a length of about 20 to 25 bases and is a kind of ncRNA (non-coding RNA) which is considered to have the function of regulating the expression of other genes. miRNA is generated through processing upon transcription into RNA and is present as a nucleic acid capable of forming a hairpin structure which suppresses the expression of a target sequence.

Since miRNA is also an inhibitory nucleic acid based on RNAi, miRNA may also be designed and synthesized in the same manner as in the case of shRNA or siRNA.

Expression vectors for RNAi may be readily prepared with a commercially available DNA/RNA synthesizer (e.g., Applied Biosystems model 394) on the basis of pMuniH1 plasmid, pSINsi vector (Takara Bio Inc., Japan), pSIF1-H1 (System Biosciences, Inc.), etc. Examples of expression vectors for RNAi include, but are not limited to, pSPB1876 (WO2004/071467). Expression vectors for RNAi may be prepared by entrusting their preparation to third parties such as Cosmo Bio Co., Ltd. (Japan), Takara Bio Inc. (Japan), Invitrogen, Promega, etc.

A method for producing a plant modified to suppress the expression of monoterpene glycosyltransferase may comprise the following steps.

(1) Step of Introducing an Expression Vector for RNAi (e.g., siRNA Expression Vector or miRNA Expression Vector) Against Monoterpene Glycosyltransferase into a Host Plant or a Portion Thereof Introduction of an expression vector for RNAi into a host plant may be accomplished in the same manner as described above in the section "3. Non-human transformant rich in monoterpene glycosides." The host plant may be any of a whole plant or a portion thereof, i.e., a plant organ (e.g., leaf, petal, stem, root, seed), a plant tissue (e.g., epidermis, phloem, parenchyma, xylem, vascular bundle, palisade tissue, spongy parenchyma) or a cultured plant cell, or alternatively, various forms of plant cells (e.g., suspension cultured cells), a protoplast, a leaf section, a callus and so on. The type of plant is also as described above in the section "3. Non-human transformant rich in monoterpene glycosides."

(2) Step of Growing the Transgenic Plant Obtained in the Above Step (1)

If the host plant used in the above step (1) is a portion of a whole plant, such as a plant organ, a plant tissue, a plant cell, a protoplast, a leaf section or a callus, the resulting transformant may be grown in an appropriate environment until a perfect whole plant is formed. With respect to techniques for growing a portion of a whole plant into a perfect whole plant, reference may be made to the descriptions in the following document: Biochemistry Experiments Vol. 41, An Introduction to Plant Cell Technology, Japan Scientific Societies Press, ISBN 4-7622-1899-5.

Upon cultivation of the thus obtained plant which is modified to suppress the expression of a gene for monoterpene glycosyltransferase, monoterpene aglycons can be produced efficiently.

6. Processed Product of a Plant Modified to Suppress the Expression of a Gene for Monoterpene Glycosyltransferase Today, not only natural flowers (e.g., soil-grown plants, potted plants, cut flowers), but also processed products of natural flowers are sold as products for plant appreciation. Due to their strong aroma, plants modified to suppress the expression of a gene for monoterpene glycosyltransferase are also very useful as materials for such processed products of natural flowers. Thus, another embodiment of the present invention is a processed product of a plant (e.g., natural flower, cut flower) modified to suppress the expression of a gene for monoterpene glycosyltransferase or a portion of the plant (e.g., leaf, petal, stem, root, seeds, bulb). Examples of such a processed product include, but are not limited to, pressed flowers, dried flowers, preserved flowers, material flowers, resin-embedded products, etc.

7. Extract of a Plant Modified to Suppress the Expression of Monoterpene Glycosyltransferase and Use Thereof In another embodiment, the present invention also provides an extract of the above plant modified to suppress the expression of monoterpene glycosyltransferase. Since the plant modified to suppress the expression of monoterpene glycosyltransferase is rich in monoterpene aglycons when compared to the wild-type counterpart, an extract of the modified plant is considered to contain monoterpene aglycons at high concentrations.

The above extract can be extracted in the same manner as described above for the extract of the transformant of the present invention.

The thus obtained extract can be provided for use in, e.g., production of foods, aromatics, pharmaceutical preparations and/or industrial raw materials (e.g., raw materials for cosmetics, soaps, etc.) according to standard practice.

In another embodiment, the present invention also provides a food, an aromatic, a pharmaceutical preparation and/or an industrial raw material (e.g., raw materials for cosmetics, soaps, etc.), each containing the above extract. Such a food, an aromatic, a pharmaceutical preparation and/or an industrial raw material, each containing the above extract, may be prepared in a routine manner. In this way, such a food, an aromatic, a pharmaceutical preparation and/or an industrial raw material, each containing the extract of the plant modified to suppress the expression of monoterpene glycosyltransferase, contain monoterpene aglycons generated by using the plant modified to suppress the expression of monoterpene glycosyltransferase.

The food, aromatic, pharmaceutical preparation and industrial raw material of the present invention are of the same type and composition as described above in the section "3. Extract of transformant and use thereof."

8. Screening Method for a Plant Rich in Terpene Glycosides or a Plant Rich in Monoterpene Aglycons The present invention provides a screening method for a plant rich in monoterpene aglycons. More specifically, the above method comprises steps (1) to (3) shown below:
(1) the step of extracting mRNA from a test plant;
(2) the step of allowing hybridization between the above mRNA or cDNA prepared from the above mRNA and a polynucleotide which is hybridizable under high stringent conditions with a polynucleotide consisting of a nucleotide sequence complementary to the polynucleotide of the present invention; and
(3) the step of detecting the above hybridization.

The above step (1) may be accomplished by extracting mRNA from a test plant. Although mRNA may be extracted from any site of the test plant, preferred are petals. Once mRNA has been extracted, cDNA may be prepared from the mRNA through reverse transcription.

The above step (2) may be accomplished as follows: a polynucleotide or oligonucleotide consisting of a nucleotide sequence complementary to the polynucleotide of the present invention is used as a probe or primer and allowed to hybridize with the mRNA extracted above under high stringent conditions. High stringent conditions are as already described above. Such a polynucleotide or oligonucleotide has a length of preferably 5 to 500 bp, more preferably 10 to 200 bp, and even more preferably 10 to 100 bp. The polynucleotide or oligonucleotide may be readily synthesized with various automatic synthesizers (e.g., AKTA oligopilot plus 10/100 (GE Healthcare)), or alternatively, its synthesis may be entrusted to a third party (e.g., Promega or Takara), etc.

When the polynucleotide consisting of a nucleotide sequence complementary to the polynucleotide of the present invention is used as a probe in the step (2), the step (3) may be accomplished by commonly used techniques for detection of hybridization, such as Southern blotting, Northern blotting (Sambrook, Fritsch and Maniatis, "Molecular Cloning: A Laboratory Manual" 2nd Edition (1989), Cold Spring Harbor Laboratory Press), microarrays (Affymetrix; see U.S. Pat. Nos. 6,045,996, 5,925,525 and 5,858,659), TaqMan PCR (Sambrook, Fritsch and Maniatis, "Molecular Cloning: A Laboratory Manual" 2nd Edition (1989), Cold Spring Harbor Laboratory Press), or fluorescent in situ hybridization (FISH) (Sieben V. J. et al., (2007-06). IET Nanobiotechnology 1 (3): 27-35). On the other hand, when the polynucleotide consisting of a nucleotide sequence complementary to the polynucleotide of the present invention is used as a primer in the step (2), the step (3) may be accomplished by PCR amplification and the subsequent analysis of the resulting amplification products by electrophoresis or sequencing (Sambrook, Fritsch and Maniatis, "Molecular Cloning: A Laboratory Manual" 2nd Edition (1989), Cold Spring Harbor Laboratory Press), etc., to detect hybridization.

A whole plant in which hybridization was more often detected can be regarded as expressing higher levels of a protein having glycosylation activity on a monoterpene compound than other whole plants, and hence such a whole plant is predicted to be rich in terpene glycosides.

On the other hand, a whole plant in which hybridization was less often detected shows lower expression of a protein having glycosylation activity on a monoterpene compound than other whole plants, and hence such a whole plant is predicted to be rich in monoterpene aglycons, and in particular to release a strong aroma during flowering.

EXAMPLES

The present invention will now be described in more detail by way of the following examples, which are not intended to limit the scope of the present invention.

Cloning of *Arabidopsis thaliana*-Derived UGT85A3 and UGT85A1 Homologs from *Humulus lupulus*

Attempts were made to isolate UGT genes from *Humulus lupulus*, which are highly homologous to genes for *Arabidopsis thaliana*-derived glycosyltransferase enzymes UGT85A3 (International *Arabidopsis thaliana* Gene No. At1g22380) and UGT85A1 (International *Arabidopsis thaliana* Gene No. At1g22400). From immature and mature cones and leaves of *Humulus lupulus* (Shinshu wase variety), RNA was extracted with a Spectrum Plant Total RNA Kit (SIGMA), followed by treatment with an Oligotex-dT30 (SEQ ID NO: 21) mRNA purification kit (Takara Bio Inc., Japan) to obtain polyA(+) RNA. This polyA(+) RNA (5 µg) was used as a template to prepare a cDNA library using a Lambda ZAP cDNA synthesis kit (cDNA synthesis kit/Uni ZAP XR vector kit/GigaPacI III Gold Packaging Extract (Agilent)) in accordance with the method recommend by the manufacturer. The prepared library was $3.11 \times 10^6$ pfu/ml. Approximately 500,000 plaques of this cDNA library were screened by using the full-length cDNA (SEQ ID NO: 9) of the *Arabidopsis thaliana* UGT85A1 gene and the full-length cDNA (SEQ ID NO: 10) of the *Arabidopsis thaliana* UGT85A3 gene as probes.

Namely, fragments amplified with the following primer sets 1 and 2 were used as screening probes to conduct plaque hybridization screening.

```
Primer set 1
CACC-NdeI-UGT85A3-Fw:
                                     (SEQ ID NO: 11)
5'-CACCCATATGGGATCCCGTTTTGTTTC-3'

XhoI-stop-UGT85A3-Rv:
                                     (SEQ ID NO: 12)
5'-CTCGAGTTACGTGTTAGGGATCTTTC-3'

Primer set 2
NdeI-AtUGT85A1-Fw
                                     (SEQ ID NO: 13)
5'-CACCCATATGGGATCTCAGATCATTCATAAC-3'

BamHI-AtUGT85A1-Rv
                                     (SEQ ID NO: 14)
5'-GGATCCTTAATCCTGTGATTTTTGTCCCAAAAG-3'
```

The probes were each labeled by PCR using a non-radioisotope DIG-nucleic acid detection system (Roche Diagnostics) under the conditions recommended by the manufacturer. A PCR reaction solution used for this purpose was prepared to contain 1 µl of template DNA (about 1 pg of the UGT85A3 expression plasmid mentioned above), 1× Taq buffer (TaKaRa Bio), 0.2 mM dNTPs, primers (0.2 pmol/µl each) and rTaq polymerase (1.25 U). This PCR reaction solution was reacted at 94° C. for 5 minutes, followed by 30 cycles of reaction at 94° C. for 1 minute, at 52° C. for 1 minute and at 72° C. for 2 minutes, and final treatment at 72° C. for 5 minutes. This PCR product was applied to a Mini Quick Spin column (Roche) to remove the primers and unreacted dNTPs, and the resulting product was used as a screening probe.

Library screening and positive clone detection were accomplished by using a non-radioisotope DIG-nucleic acid detection system (Roche Diagnostics) in accordance with the method recommend by the manufacturer. Hybridization was conducted overnight at 37° C. in 5×SSC containing 30% formamide, and the membranes were washed with 5×SSC and 1% SDS at 55° C. for 20 minutes. Approximately 500,000 plaques were screened. After secondary screening, the resulting positive clones were analyzed with a DNA Sequencer model 3100 (Applied Biosystems) by primer walking with synthetic oligonucleotide primers, thus obtaining cDNA sequences. The resulting cDNA sequences were analyzed for homology using the Blastx program (http://blast.ncbi.nlm.nih.gov/Blast.cgi) to thereby obtain *Humulus lupulus*-derived homolog genes (HlUGT) of *Arabidopsis thaliana* UGT85A3 and UGT85A1.

The resulting HlUGT genes are as follows: HlUGT119 (CDS sequence: SEQ ID NO: 1, amino acid sequence: SEQ ID NO: 2), HlUGT127 (CDS sequence: SEQ ID NO: 3, amino acid sequence: SEQ ID NO: 4), HlUGT279 (CDS sequence: SEQ ID NO: 5, amino acid sequence: SEQ ID NO: 6) and HlUGT251 (CDS sequence: SEQ ID NO: 7, amino acid sequence: SEQ ID NO: 8).

To clarify the monoterpene glycosylation activity of these four types of HlUGT enzymes, these enzymes were expressed in *E. coli* cells. For construction of expression vectors, the primer sets shown below were used for PCR amplification.

```
Primer set for amplification of HlUGT119
Forward:
                             (SEQ ID NO: 15)
5'-CACCCATATGACCATGGAAACTAAGCCTCA-3'

Reverse:
                             (SEQ ID NO: 16)
5'-CTCGAGTTATGGTTTTGATGATGGCACCAAAAC-3'

Primer set for amplification of H1UGT127
Forward:
                             (SEQ ID NO: 15)
5'-CACCCATATGACCATGGAAACTAAGCCTCA-3'

Reverse:
                             (SEQ ID NO: 17)
5'-CTCGAGTTATGGCTTTGATGATGGCACCAAAAC-3'

Primer set for amplification of H1UGT279
Forward:
                             (SEQ ID NO: 15)
5'-CACCCATATGACCATGGAAACTAAGCCTCA-3'

Reverse:
                             (SEQ ID NO: 18)
5'-GGATCCTTAGGGTTTTGAGAGTGGAACCAATAC-3'

Primer set for amplification of HlUGT251
Forward:
                             (SEQ ID NO: 19)
5'-CACCCATATGGGTTCAATCAGCGAAATGATG-3'

Reverse:
                             (SEQ ID NO: 20)
5'-GGATCCTTAGTCCCTACCATCAAAGC-3'
```

A PCR reaction solution (50 μl) was prepared to consist of *Humulus lupulus*-derived cDNA (1 μl), 1× ExTaq buffer (TaKaRaBio), 0.2 mM dNTPs, primers (0.4 pmol/μl each) and ExTaq polymerase (2.5 U). The PCR reaction was accomplished by incubation at 94° C. for 3 minutes and the subsequent amplification in which reactions at 94° C. for 1 minute, at 50° C. for 1 minute and at 72° C. for 2 minutes were repeated for 30 cycles in total. The PCR products were electrophoresed on a 0.8% agarose gel and stained with ethidium bromide, thereby resulting in an amplified band at a size of approximately 1.4 kb predicted from each template DNA.

These PCR products were subcloned into pENTR-TOPO Directional vector (Invitrogen) in accordance with the method recommend by the manufacturer. The clones were analyzed with a DNA Sequencer model 3100 (Applied Biosystems) by primer walking with synthetic oligonucleotide primers, thus confirming that there was no PCR-induced mutation in the inserted fragment.

Subsequently, the resulting four HlUGT genes were each inserted into an Invitrogen *E. coli* expression vector pET15b (Novagen) in accordance with the method recommend by the manufacturer to prepare *E. coli* expression plasmids, by which HlUGT119, HlUGT127, HlUGT279 and HlUGT251 were each expressed as a fusion protein with HisTag.

The *E. coli* expression plasmids obtained above were each used to transform *E. coli* strain BL21(DE3) in a standard manner. The resulting transformants were each cultured overnight at 37° C. under shaking conditions in 4 ml of a 50 μg/ml ampicillin-containing LB medium (10 g/l typtone pepton, 5 g/l yeast extract, 1 g/l NaCl). After reaching the resting phase, each cultured solution (4 ml) was inoculated into a medium of the same composition (80 ml) and cultured at 37° C. under shaking conditions. At the time point where the cell turbidity (OD600) reached about 0.5, IPTG was added at a final concentration of 0.5 mM, followed by culturing at 18° C. for 20 hours under shaking conditions.

The following manipulations were all performed at 4° C. Each cultured transformant was collected by centrifugation (5,000×g, 10 min) and then added to and suspended in Buffer S [20 mM HEPES buffer (pH 7.5), 20 mM imidazole, 14 mM β-mercaptoethanol] at 1 ml/g cell. Subsequently, the suspension was homogenized by ultrasonication (15 sec, repeated 8 times) and then centrifuged (15,000×g, 15 min). The resulting supernatant was collected as a crude enzyme solution. The crude enzyme solution was loaded onto a His SpinTrap column (GE Healthcare) which had been equilibrated with Buffer S, followed by centrifugation (70×g, 30 sec). After washing with the buffer, proteins bound to the column were eluted stepwise with 5 ml each of Buffer S containing 100 mM and 500 mM imidazole. Each elution fraction was subjected to buffer replacement with 20 mM HEPES buffer (pH 7.5), 14 mM β-mercaptoethanol through a Microcon YM-30 unit (Amicon) (magnification of dialysis: ×1000).

When the purified proteins were separated by SDS-PAGE, protein expression was confirmed at the size predicted from each cDNA (FIG. 1). In FIG. 1, the arrow and the boxed bands represent the eluted histidine tag-fused HlUGT proteins. The lanes represent, from the left, a size marker, HlUGT119, HlUGT127, UlUGT279 and HlUGT251. It is indicated that the amount of purified expressed protein is lower in HlUGT251 than in the other UGTs.

Next, these proteins were used to test their reactivity with monoterpenes by LC-MS analysis.

Standard enzyme reaction conditions are as follows. A reaction solution (2 mM UDP-glucose, 0.2 mM sugar acceptor substrate, 100 mM potassium phosphate buffer (pH 7.5), 25 μl purified VvUGT enzyme solution) was prepared in a volume of 50 μl with distilled water and reacted at 30° C. for 1 hour.

The enzyme reaction solution (5 μl) was analyzed by LC-MS under the following conditions.
LC Conditions
Column: CAPCELL PAK C18-UG120 (2.0 mm I.D.×150 mm)
Mobile phase: A: water (containing 0.05% formic acid), B: acetonitrile
Gradient: linear concentration gradient of B from 15% to 90% over 15 minutes
Flow rate: 0.2 ml per minute
Column oven: 40° C.
MS Conditions
ESI (negative mode)
SIM mode: (m/z 315, 338, 361, 363, 331, 354, 377, 429, etc.)

The above LC-MS analysis was conducted for each of HlUGT119, HlUGT127, HlUGT279 and HlUGT251.

Figure 2:
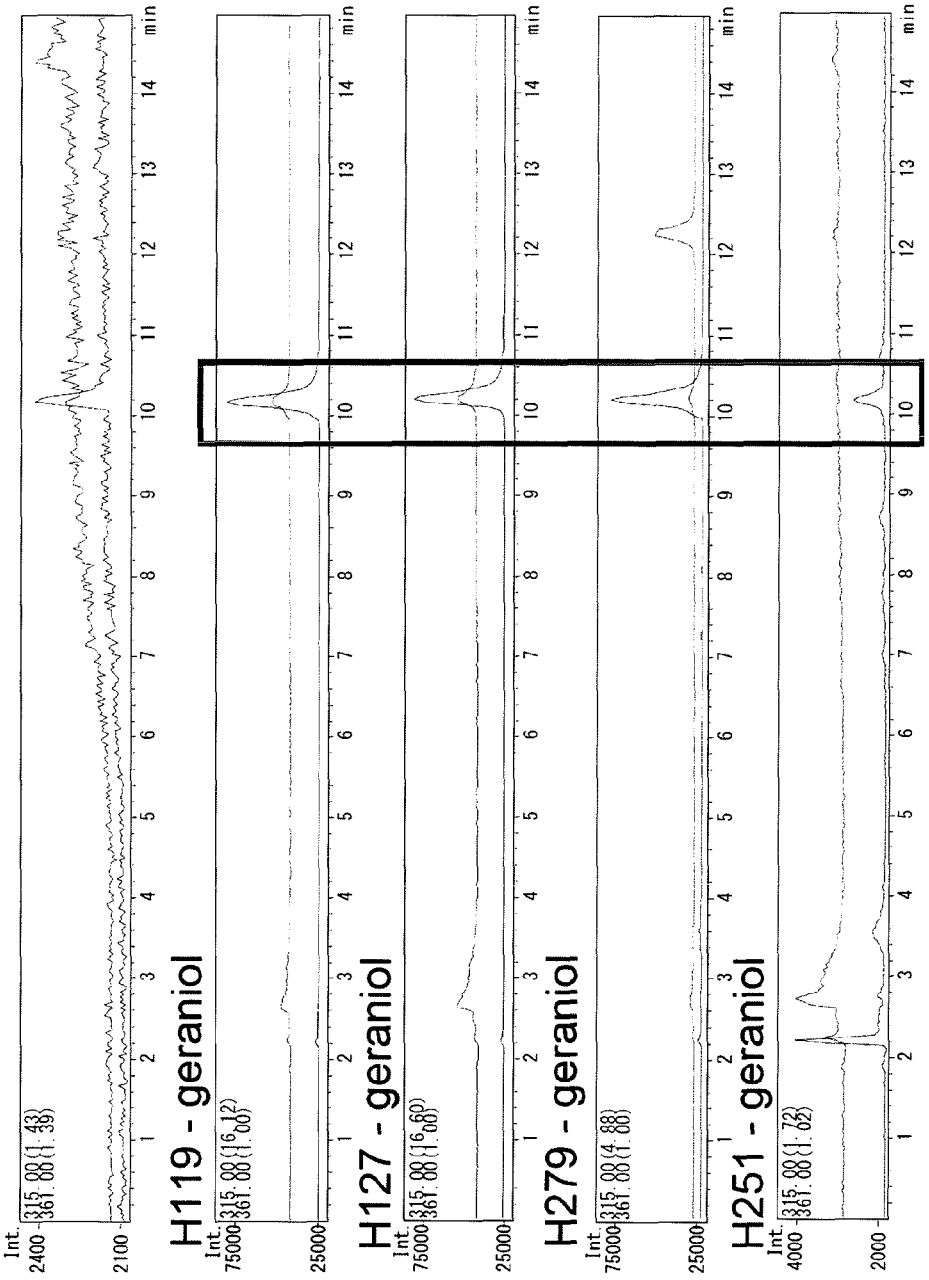
FIG. 2 shows the geraniol glycosylation activity of *Humulus lupulus* HlUGT recombinant proteins.
Figure 3:
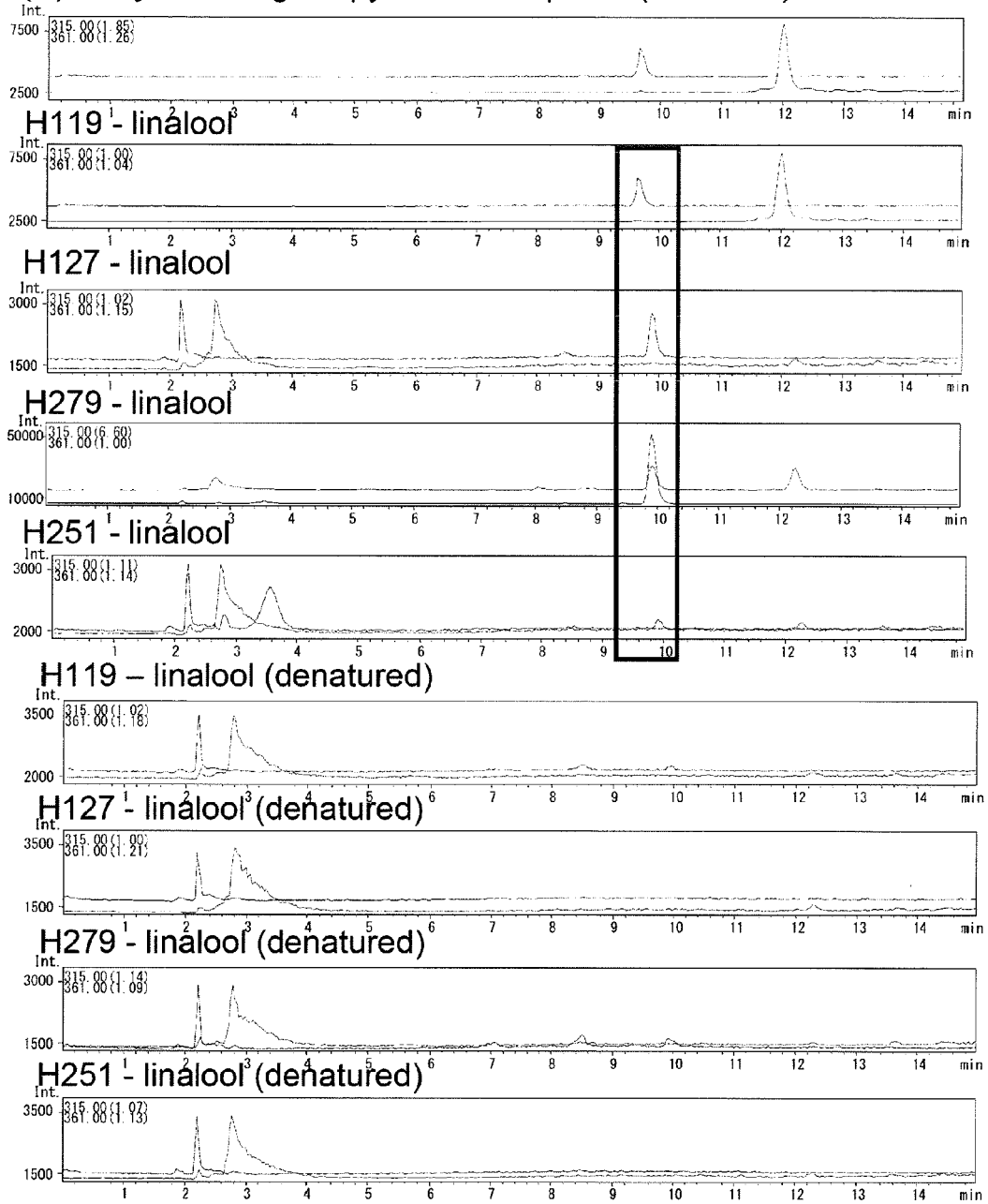
FIG. 3 shows the linalool glycosylation activity of *Humulus lupulus* HlUGT recombinant proteins.

As a result, four types of HlUGT were all found to show monoglycosylation activity on geraniol and linalool (activity on geraniol: FIG. 2, activity on linalool: FIG. 3). In FIG. 2, the individual panels show the results of LC-MS analysis obtained for, from the top, geraniol glycoside (reference standard), a reaction solution of geraniol and HlUGT119, a reaction solution of geraniol and HlUGT127, a reaction solution of geraniol and HlUGT279, and a reaction solution of geraniol and HlUGT251. In FIG. 2, the boxed peaks each represent the enzyme reaction product (geraniol glycoside). Likewise, in FIG. 3, the individual panels show the results of LC-MS analysis obtained for, from the top, linalool glycoside (reference standard), a reaction solution of linalool and HlUGT119, a reaction solution of linalool and HlUGT127, a reaction solution of linalool and HlUGT279, a reaction solution of linalool and HlUGT251, a reaction solution of linalool and thermally denatured HlUGT119, a reaction solution of linalool and thermally denatured HlUGT127, a reaction solution of linalool and thermally denatured HlUGT279, and a reaction solution of linalool and thermally denatured HlUGT251. In FIG. 3, the boxed peaks each represent the enzyme reaction product (linalool glycoside).

These four types of UGT enzymes were confirmed to be novel enzymes having glycosylation activity to give monoterpene alcohols because no product was observed in their respective thermally denatured proteins. Among these four enzymes, HlUGT251 showed a smaller amount of product under the same reaction conditions. This would be because the amount of expressed protein is extremely lower in HlUGT251 than in the other three enzymes (FIG. 1).

INDUSTRIAL APPLICABILITY

According to the present invention, one glucose molecule can be transferred to monoterpenes in vitro or by introducing the gene of the present invention into host cells, and hence the present invention is very useful in allowing more simple production or reduction of terpene glycosides, which may contribute to development of novel functional food materials and/or molecular breeding of secondary metabolites, etc.

Sequence Listing Free Text
SEQ ID NO: 11: synthetic DNA
SEQ ID NO: 12: synthetic DNA
SEQ ID NO: 13: synthetic DNA
SEQ ID NO: 14: synthetic DNA
SEQ ID NO: 15: synthetic DNA
SEQ ID NO: 16: synthetic DNA
SEQ ID NO: 17: synthetic DNA
SEQ ID NO: 18: synthetic DNA
SEQ ID NO: 19: synthetic DNA
SEQ ID NO: 20: synthetic DNA

The invention claimed is:

1. A recombinant protein which consists of an amino acid sequence with substitution, insertion and/or addition of 1 to 70 amino acids in the amino acid sequence shown in SEQ ID NO: 2, 4 or 6 and which has glycosylation activity on a monoterpene compound.

2. The recombinant protein according to claim 1, wherein the monoterpene compound is geraniol or linalool.

3. A polynucleotide of any one selected from the group consisting of (a) to (e) shown below:
 (a) a polynucleotide containing the nucleotide sequence shown in SEQ ID NO: 1, 3 or 5;
 (b) a polynucleotide encoding a recombinant protein which consists of the amino acid sequence shown in SEQ ID NO: 2, 4 or 6;
 (c) a polynucleotide encoding a recombinant protein which consists of an amino acid sequence with deletion, substitution, insertion and/or addition of 1 to 70 amino acids in the amino acid sequence shown in SEQ ID NO: 2, 4 or 6 and which has glycosylation activity on a monoterpene compound;
 (d) a polynucleotide encoding a recombinant protein which has an amino acid sequence sharing a sequence identity of 85% or more with the amino acid sequence shown in SEQ ID NO: 2, 4 or 6 and which has glycosylation activity on a monoterpene compound; and (e) a polynucleotide which is hybridizable under high stringent conditions with a polynucleotide consisting of a nucleotide sequence complementary to the nucleotide sequence shown in SEQ ID NO: 1, 3 or 5 and which encodes a recombinant protein having glycosylation activity on a monoterpene compound, wherein the polynucleotide is inserted into an expression vector.

4. A non-human transformant transformed with the polynucleotide according to claim 3.

5. The transformant according to claim 4, which is a whole plant.

6. An extract of the transformant according to claim 4, wherein the extract contains monoterpene glycosides at higher concentrations than a wild-type counterpart.

7. A food, an aromatic, a pharmaceutical preparation or an industrial raw material, which comprises the extract according to claim 6.

8. A method for producing a protein having glycosylation activity on a monoterpene compound, which comprises culturing the non-human transformant according to claim 4.

9. A method for producing a monoterpene glycoside, which comprises reacting
   (1) a recombinant protein of any one selected from the group consisting of (a) to (c) shown below:
      (a) a recombinant protein which consists of the amino acid sequence shown in SEQ ID NO: 2, 4 or 6;
      (b) a recombinant protein which consists of an amino acid sequence with deletion, substitution, insertion and/or addition of 1 to 70 amino acids in the amino acid sequence shown in SEQ ID NO: 2, 4 or 6 and which has glycosylation activity on a monoterpene compound; and
      (c) a recombinant protein which has an amino acid sequence sharing a sequence identity of 85% or more with the amino acid sequence shown in SEQ ID NO: 2, 4 or 6 and which has glycosylation activity on a monoterpene compound,
   (2) a UDP-sugar, and
   (3) a monoterpene compound
to cause glycosylation of the monoterpene compound.

10. The method according to claim 9, wherein the UDP-sugar is UDP-glucose.

11. The method according to claim 9, wherein the monoterpene compound is geraniol or linalool.

* * * * *